(12) United States Patent
Zuker et al.

(10) Patent No.: US 7,867,721 B2
(45) Date of Patent: *Jan. 11, 2011

(54) IN VITRO METHOD FOR IDENTIFYING A COMPOUND USING AN EUKARYOTIC MECHANOSENSORY TRANSDUCTION CHANNEL

(75) Inventors: Charles S. Zuker, San Diego, CA (US); Richard G. Walker, La Jolla, CA (US); Aarron Willingham, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 11/703,343

(22) Filed: Feb. 6, 2007

(65) Prior Publication Data

US 2009/0075294 A1    Mar. 19, 2009

Related U.S. Application Data

(60) Continuation of application No. 10/369,978, filed on Feb. 18, 2003, now abandoned, which is a division of application No. 09/392,812, filed on Sep. 9, 1999, now Pat. No. 6,537,778.

(51) Int. Cl.
*G01N 33/53* (2006.01)
*C12N 5/00* (2006.01)
*C07K 14/00* (2006.01)

(52) U.S. Cl. .................. 435/7.2; 435/325; 530/350

(58) Field of Classification Search .......... None
See application file for complete search history.

(56) References Cited

U.S. PATENT DOCUMENTS 5,824,306 A    10/1998    Tang et al.

OTHER PUBLICATIONS

Corey, et al., New TRP channels in hearing and mechanosensation, 2003, Cell, vol. 39, paes 585-588.

Garcia-Anoveros, J, et al. "The Molecules of Mechanosensation," Annu. Rev. Neurosci., 1997, 20:567-594.
Gillespie, et al., "Have we found the tip link, transduction channel, and gating spring of the hair cell?" 2005, Current Opinion in Neurobiology, vol. 15, pp. 389-396.
Hudspeth, A.J., "How the ear's works work," nature, 1989, 341:397-404.
Kernan, M. et al., "Genetic Dissection of Mechanosensory Transduction: Mechanoreception-Defective Mutations of Drosphila," Neuron, 1994, 12:1195-1206.
Liman, et al. "TRP2: A candidate transduction channel for mammalian pheromone sensory signaling." Proc. Natl. Acad. Sci., USA. May 1999, vol. 96, pp. 5791-5796.
Mikayama, T. "Molecular cloning and functional expression of a cDNA encoding glycosylation-inhibiting factor." Proc. Natl. Acad. Sci. USA vol. 90, pp. 10056-10060, 1993.* .
Montell, C., "TRP trapped in fly signaling web," Current Opinion in Neurobiology, 8:389-397 (1998).
Sukharev, S.I., et al., "A large-conductance mechanosensitive channel in *E. coli* encoded by mscL alone," nature, 1994, 368:265-268.
Vannier, et al. Mouse trp2, the homologue of the human trpc2 pseudogene, encodes mTrp2, a store depletion-activated capacitative Ca2+ entry channel. Proc. Natl. Acad. Sci. USA. Mar. 1999, vol. 96, pp. 2060-2064.
Voet, et al. Biochemistry. 1990. John Wiley & Sons, Inc.. pp. 126-128 and 228-234.
Wissenbach, et al. Structure and mRNA expression of a bovine trp homologue related to mammalian trp2 transcripts. FEBS letters. 1998, vol. 429, pp. 61-66.

*Primary Examiner*—Robert Landsman
*Assistant Examiner*—Ian Dang
(74) *Attorney, Agent, or Firm*—Townsend and Townsend and Crew LLP

(57) ABSTRACT

The present invention provides, for the first time, nucleic acids encoding a eukaryotic mechanosensory transduction channel (MSC) protein. The proteins encoded by these nucleic acids form channels that can directly detect mechanical stimuli and convert them into electrical signals. These nucleic acids and the proteins they encode can be used as probes for sensory cells in animals, and can be used to diagnose and treat any of a number of human conditions involving inherited, casual, or environmentally-induced loss of mechanosensory transduction activity.

7 Claims, 3 Drawing Sheets

FIG. 1A

```
Drosophila   ----------  ----------  ----------  ----------  ----------  ----------
C.elegans    MSRSEKCLTVRKRET  RSTSVTRAEWFTGKK  MDAAKNAFDLLTTDT  IPTDRPPLRRSSTHL  QIGKNSRIIFVPKQP  SRDSVTPPDRLLGKP Drosophila   ----------  ----------  ----------  ----------  ----------  ----------
C.elegans    LFRESLTSHASSHEE  MSSEDLAMADPQTKI  LYFAKRDEWANVESE  IETIKRSDFSMADNH  GFTAFLLAVKAGKDQ  IVDKMIRKGARVDYS Drosophila   ----------  ----------  ----------  ----------  ----------  ----------
C.elegans    TKDGRNATHIAAMYS  GVETLELILKRYSEL  LRKGAGPKKQLAIHV  ACERKSKKAFPIVKR  ILEDTDQRMAEDGDG  SLPIHLAFKFGNVNI Drosophila   ----------  ----------  ----------  ----------  ----------  ----------
C.elegans    VELLLSGPSDEQTRK  ADGNGDTLLHLAARS  GNIEAVRTAIAAGCD  NANVQNRVGRTPLHE  CLTVTGTQKGYVAEV  GDQNMLKIMFKLRAD Drosophila   ----------RTPMHLA  AENGHAHVIEILADK  FKASIFERTKDGSTL  MHIASLNGHAECATM  LFKKGVYLHMPNKDG  ARSIHTAAAYGHTGI
C.elegans    ANIHDKEDKTPVHVA  AERGDTSMVESLIDK  FGGSIRARTRDGSTL  LHIAACSGHTSTALA  FLKR-VPLFMPNKKG  ALGLHSAAAAGFNDV Drosophila   INTLLQKGEKVDVTT  -NNYTALHIAVESAK  PAVVETLLGFGADVH  VRGGKLRETPLHIAA  RVKDGDRCALMLLKS  GASPNLTTDDCLTPV
C.elegans    VKMLIARGTNVDVRT  RDNYTALHVAVQSGK  ASVVETLLGSGADIH  VKGG---E------  -LMDGETC------  ----------L Drosophila   HVAARHGNLATLMQL  LEDEGDPLYKSNTGE  TPLHMACRACHPDIV  RHLIETVKEKHGPDK  ATTYINSVNEDGATA  LHYTCQITKEEVKIP
C.elegans    HIAARSGNKD-IMLL  LDENADSKISSKIGE  TPLQVAAKSCNFEAA  SMILKHLSEVLTQEQ  LKEHVNHRTNDGFTA  LHYAAEIEQRQLHFP Drosophila   ESDKQIVRMLLENGA  DVTLQTKTALETAFH  YCAVAGNNDVLMEMI  SHMNPTDIQKAMNRQ  SSVGWTPLLIACHRG  HMELVNNLL-----
C.elegans    GEDAKLVNLLIDYGG  MVEMPSLNANETAMH  MAARSGNQAVLLAMV  NKIGAGAVQIVQNKQ  SKNGWSPLLEACARG  HSGVANILLKVLVLC Drosophila   ----------  VGPGPGPGPRLQGRG  YWTRTRARVTVPWLQ  YQGYWARTRTRTRAR  ATGPGLQDQGYWART  RTRTKVTVPRLLGDH  HARIDVFDEMGRTAL
C.elegans    ----------  ----------  ----------  ----------  ----------AN  HARVDVFDTEGRSAL Drosophila   HLAAERGYLHVCDAL  LTNKAFINSKSRVGR  TALHLAAMNGFTHLV  KFLIKDHNAVIDILT  LRKQTPLHLAAASGQ  MEVCQLLLELGANID
C.elegans    HLAAFNGHLSLVHLL  LQHKAFVNSKSKTGE  APLHLAAQHGHVKVV  NVLVQDHGAALEAIT  LDNQTALHFAAKFGQ  LAVSQTLLALGANPN
```

FIG. 1B

```
Drosophila  ATDDLGQKPIHVAAQ NNYSEVAKLFLQQHP ---SLVNATSKDGNT CAHIAAMQGSVKVIE ELMKFDRSGVISARN KLTDATPLQLAAEGG
C.elegans   ARDDKGQTPLHLAAE NDFPDVVKLFLKMRN NNRSVLTAIDHNGFT CAHIAAMKGSLAVVR ELMMIDKPMVIQAKT KTLEATTLHMAAAGG Drosophila  HADVVKALVRAGASC TEENKAGFTAVHLAA QNGHGQVLDVLKSTN SLRINSKKLGLTPLH VAAYYGQADTVRELL TSVPATVKSETPTG-
C.elegans   HANIVKILLENGANA EDEN-SGMTALHLGA KNGFISILEAFDKIL WKRC-SRKTGLNALH IAAFYGNSDFVNEML KHVQATVRSEPPIYN Drosophila  QSLFGDLGTESGMTP LHLAAFSGNENVVRL LLNSAGVQVDAATIE NMHGHIQMVEILLGQ GAEINATDRNGWTPL HCAAKAGHLEVVKLL
C.elegans   HHVNKEFSTEYGFTP LHLAAHSGHDSLVRM LLN-QGVQVDATSTT MMS------------ --------------- ---------------

Drosophila  CEAGASPKSETNYGC AAIWFAASEGHNEVL RYLMNKEHDTYGLME DKRFVYNLMVVSKNH NNKPIQEFVLVSPAP VDTAAKLSNIYIVLS
C.elegans   --------------- --------------- --------------- E-------------- ----K---------- -------E-------

Drosophila  TKKERAKDLVAAGKQ CEAMATELLALAAGS DSAGKILQATDKRNV EFLDVLIENEQKEVI AHTVVQRYLQELWHG SLTWASWKILLLLVA
C.elegans   --KERAKDLLNVAVF SENMAVELLITATEY N-AALLLKAKDNRGR PLLDVLIENEQKEVV SYASVQRYLTEVWTA RVDWSFGKFVAFSLF Drosophila  FIVCPPVWIGFTFPM GHKFNKVPIIKFMSY LTSHIYLMIHLSIVG ITPIYPVLRLSLVPY WYEVGLLIWLSGLLL FELTNPSDKSGLGSI
C.elegans   VLICPPAWFYFSLPL DSRIGRAPIIKFVCH IVSHVYFTILLTIVV LNITHKYEVTSVVPN PVEWLLLWLSGNLV  SELSTVGGGSGLGIV Drosophila  KVLVLLLGMAGVGVH VSAFLFVS------- -----KEYWPTLVYCR NQCFALAFLLACVQI LDFLSFHHLFGPWAI IIGDLLKDLARFLAV
C.elegans   KVLILVLSAMAIAVH VLAFLLPAVFLTHLD NDEKLHFARTMLYLK NQLFAFALLFAFVEY LDFLTVHHLFGPWAI II---MYDLARFLVI Drosophila  LAIFVGFSMHIVAL NQSFANFSPEDLRSF EKKNRNRGYFSDMEQ MTCPHPDLRRWRIMS IVASANSDESTRTTF PGGTSTSPHSLLEIP
C.elegans   LMLFVAGFTLHVTSI ------FQP------ --------------- --------------- --AYQPVDE------ ---------------

Drosophila  SPCMHVDVFIQSIQT KIKQSISNIDITNAR LPGAFSLRRLPTTKF CTIETIETDRIESIT KNDNATDTDYRCSYM LGPMTPFLAFERLFF
C.elegans   --------------- --------------- --------------- ---DSAELMRLASPS Q-------------- ---------TLEMLFF Drosophila  AVFGQTTTLDINPMR HLRPEWTEVLFKFVF GIYLLVSVVVLINLL IAMMSDTYQRIQMN- -RNWGLVDRTNQRNK KKKKNHIIESTNPTW
C.elegans   SLFGLVEP-DSMPPL HLVPDFAKIILKLLF GIYMMVTLIVLINLL IAMMSDTYQRIQAQS DKEWKFGRAILIRQM NKK------SATPSP
```

FIG. 1C

```
Drosophila  ASVIFLFFKIISTPA NICVLSGGVYLYLYL YLEMYLWVSDTVRMH PINSFELLFFAVFGQ TTTEQTQVDKIKNVA TPTQPYWVEYLFKIV
C.elegans   INMLTKLIIVLRVAW RNRGK-APLSTPLAS FRCMTRKAQDDLRFE EN----IDAFSMGGGQ --------QGRQ SPTNEGRGQ------

Drosophila  FGIYMLVSVVVLINL LIAMMSDTYQRIQAQ SDIEWKFGLSKLIRN MHRTTTAPSPLNLVT TWFMWIVEKVKVKSQ VTKVAFQPLSLCLSL
C.elegans   --------QE--L GNSADWN------IE TVIDWRKIVSMYYQA NGKLTDGRTKEDVD- --LAMAVPTSFIKPQ G------PDTTCR--

Drosophila  SIRILYPVSYTCFHI CMKKKKRPSLVQMMG IRQASPRTKAGAKWL SKIKKSVALSQVHLS PLGSQASFSQANQNR IENVADWEAIAKKYR
C.elegans   -----PIDYTWLRL CKTKS-------HG SGLSIVRRKTRGKIV YSTRTNTSVLQINSS --------R-NAPK IYLRYGRAKIAHFFF Drosophila  ALVGDEEGGSLKDSD AESGSQEGSGGQQPP AQVGRRAIKATLADT TKSKLHLSLQTILPD YLYLFSTIQASVLLC TLGMVFSDSGTHFFW
C.elegans   TST------TLKG-- ---GAFMWHG----- --------------- --------------- ----LAARLCKIRVD HM-------------

Drosophila  FNWSMGKSD  1704
C.elegans   ---------  1709
```

IN VITRO METHOD FOR IDENTIFYING A COMPOUND USING AN EUKARYOTIC MECHANOSENSORY TRANSDUCTION CHANNEL

CROSS-REFERENCES TO RELATED APPLICATIONS

This application is a continuation of U.S. application Ser. No. 10/369,978, filed Feb. 18, 2003, now abandoned which is a divisional of U.S. application Ser. No. 09/392,812, filed Sep. 9, 1999, which is now U.S. Pat. No. 6,537,778. The contents of each are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Grant No. DC03160, awarded by the National Institutes of Health. The Government has certain rights in this invention.

FIELD OF THE INVENTION

This invention provides isolated nucleic acid and amino acid sequences of a novel family of eukaryotic mechanosensory ion channels that are designated mechanosensory transduction channels (MSC).

BACKGROUND OF THE INVENTION

The ability to detect mechanical stimuli is an essential and prevalent characteristic of living organisms, and is found from bacteria to simple metazoans to the most complex of mammals. Indeed, the ability to detect mechanical stimuli and convert them into electrical signals forms the basis of many central aspects of animal life, such as light touch, heavy touch, proprioception, baroreception, balance, and the crown jewel, hearing. Even the ability of cells to stop growing when in contact with neighboring cells is likely dependent on mechanical stimuli. Not surprisingly, therefore, numerous human conditions result at least in part from an inability to detect mechanical stimuli, such as Meniere's Disease, sensorineural deafness, blood pressure disorders, and various types of cancers.

In general, the variety of known mechanosensory modalities are thought to be mediated by mechanically-gated cation channels present within the membrane of receptor cells. This view has come in large part from detailed studies into the physiology of mechanosensation using various cell types involved in mechanosensory detection, such as the hair cells of the vertebrate inner ear, single-celled ciliates such as Paramecium, or the sensory neurons of Drosophila (see, e.g., Kernan et al., Neuron 12:1195-1206 (1994)). In Drosophila, the dendrite of the sensory neuron is enclosed in a cavity filled with a specialized receptor lymph, which is unusually rich in potassium ions, and is functionally equivalent to the potassium-rich endolymph of the vertebrate cochlea. These potassium ions produce a transepithelial potential difference, with the apical side of the epithelium being positively charged. Mechanical stimulation of the bristle, which is adjacent to the sensory neuron, generates a mechanoreceptor potential within the neuron, detectable as a negative deflection of the transepithelial potential, which reflects the flow of cations from the receptor lymph into the sensory neuron.

Activation of the hair cells of vertebrates also result in the influx of cations into cells (see, e.g., Hudspeth, Nature, 341: 397-404 (1989)). Each hair cell has a number of specialized microvillar structures, called stereocilia, whose deflection results in the activation of a putative channel present on the surface of the cell. Interestingly, electrophysiological studies have suggested that these cells contain a similar number of receptor channels as they do stereocilia, suggesting that perhaps each receptor channel is coupled to a single stereocilium. In addition, studies of the kinetics of hair-cell activation have suggested that the putative mechanosensory receptors are directly stimulated by mechanical force, resulting in the direct opening of the channel without the involvement of second messengers.

Despite the great importance of mechanosensation for animal behavior and health, and the detailed electrophysiological understanding that has been gained from the above-described studies, almost nothing is known about the molecular basis of mechanosensory detection in eukaryotes. Several mutations and distantly related molecules involved in this process have, however, been found. In Drosophila, for example, a number of mutations have been isolated that disrupt mechanoreception, resulting in a variety of phenotypes such as reduced locomotor activity, total uncoordination, and even death (Kernan et al., Neuron 12:1195-1206 (1994)). Also, mutations have been identified in the nematode C. elegans that result in a loss of sensitivity to gentle touch (reviewed in Garcia-Aanoveros & Corey, Ann. Rev. Neurosci. 20:567-594 (1997)). In addition, a prokaryotic mechanosensory channel has been identified (Sukarev et al., Nature 368: 265-268 (1994)). Still, despite these advances, the principle molecule of the mechanosensory transduction process in eukaryotes, the mechanically gated channel, has yet to be isolated or identified.

The identification and isolation of eukaryotic mechanosensory transduction channels would allow for the development of new methods of pharmacological and genetic modulation of mechanosensory transduction pathways. For example, availability of mechanosensory transduction channel proteins would permit screening for high-affinity agonists, antagonists, and modulators of mechanosensation in animals. Such molecules could then be used, e.g., in the pharmaceutical industry, to treat one or more of the many human conditions involving loss or hyperactivation of mechanosensation. In addition, the determination of nucleotide and amino acid sequences of mechanosensory transduction channels associated with a human condition would provide new tools for the diagnosis and/or treatment, e.g., gene-based treatment, of the condition.

SUMMARY OF THE INVENTION

The present invention provides for the first time nucleic acids encoding a eukaryotic mechanosensory transduction protein. The nucleic acids and the polypeptides they encode are referred herein as mechanosensory channel (MSC) nucleic acids and proteins. In vivo, MSC proteins form mechanosensory transduction channels that play a central role in many critical processes such as hearing, proprioception, and tactile sensation.

In one aspect, the present invention provides an isolated nucleic acid encoding a mechanosensory transduction protein, the protein having at least one of the following characteristics: (i) comprising greater than about 70% amino acid sequence identity to SEQ ID NO:2 or SEQ ID NO:4; (ii) comprising an amino acid sequence selected from the group consisting of SEQ ID NO:7, SEQ ID NO:8, and SEQ ID NO:9; or (iii) specifically binding to polyclonal antibodies generated against a polypeptide comprising an amino acid sequence of SEQ ID NO:2 or SEQ ID NO:4; wherein the protein does not comprise the polypeptide sequence of SEQ ID NO:6.

In one embodiment, the nucleic acid encodes a polypeptide comprising the amino acid sequence of SEQ ID NO:2 or SEQ ID NO:4. In another embodiment, the nucleic acid comprises a nucleotide sequence of SEQ ID NO:1 or SEQ ID NO:3, but not SEQ ID NO:5.

In another embodiment, the nucleic acid selectively hybridizes under moderately stringent wash conditions to a nucleic acid comprising a nucleotide sequence of SEQ ID NO:1 or SEQ ID NO:3. In another embodiment, the nucleic acid selectively hybridizes under stringent wash conditions to a nucleic acid comprising a nucleotide sequence of SEQ ID NO:1 or SEQ ID NO:3, but not SEQ ID NO:5.

In another embodiment, the nucleic acid is amplified by primers that selectively hybridize under stringent hybridization conditions to the same sequence as degenerate primer sets encoding an amino acid sequence selected from the group consisting of: LDVLIENEQKEV (SEQ ID NO:7), HHLFGPWAIII (SEQ ID NO:8), and VLINLLIAMMSD-TYQRIQ (SEQ ID NO:9).

In another embodiment, the nucleic acid is less than 120 kb. In another embodiment, the nucleic acid is less than 90 kb. In another embodiment, the nucleic acid is less than 60 kb. In another embodiment, the nucleic acid is less than 30 kb. In another embodiment, the nucleic acid is less than 10 kb. In another embodiment, the nucleic acid sequence encoding the MSC protein is isolated away from its genomic neighbors.

In another aspect, the present invention provides an expression cassette comprising a nucleic acid encoding a mechanosensory transduction protein, the protein having at least one of the following characteristics: (i) comprising greater than about 70% amino acid sequence identity to SEQ ID NO:2 or SEQ ID NO:4; (ii) comprising an amino acid sequence selected from the group consisting of SEQ ID NO:7, SEQ ID NO:8, and SEQ ID NO:9; or (iii) specifically binding to polyclonal antibodies generated against a polypeptide comprising an amino acid sequence of SEQ ID NO:2 or SEQ ID NO:4; wherein the protein does not comprise the polypeptide sequence of SEQ ID NO:6.

In another aspect, the present invention provides an isolated eukaryotic cell comprising the expression cassette.

In one aspect, the present invention provides an isolated nucleic acid encoding an extracellular domain of a mechanosensory transduction protein, the extracellular domain comprising greater than about 70% amino acid sequence identity to an extracellular domain of SEQ ID NO:2 or SEQ ID NO:4, wherein the extracellular domain does not comprise an extracellular domain of SEQ ID NO:6.

In one embodiment, the extracellular domain is fused to a heterologous polypeptide, thereby forming a chimeric polypeptide. In another embodiment, the extracellular domain comprises an amino acid sequence of an extracellular domain of SEQ ID NO:2 or SEQ ID NO:4.

In another aspect, the present invention provides an isolated mechanosensory transduction protein, the protein having at least one of the following characteristics: (i) comprising greater than about 70% amino acid sequence identity to SEQ ID NO:2 or SEQ ID NO:4; (ii) comprising an amino acid sequence selected from the group consisting of SEQ ID NO:7, SEQ ID NO:8, and SEQ ID NO:9; or (iii) specifically binding to polyclonal antibodies generated against a polypeptide comprising an amino acid sequence of SEQ ID NO:2, or SEQ ID NO:4; wherein the protein does not comprise the amino acid sequence of SEQ ID NO:6.

In one embodiment, the protein comprises the amino acid sequence of SEQ ID NO:2 or SEQ ID NO:4.

In another aspect, the present invention provides an isolated polypeptide comprising an extracellular domain of a mechanosensory transduction protein, the extracellular domain comprising greater than about 70% amino acid sequence identity to an extracellular domain of SEQ ID NO:2 or SEQ ID NO:4, wherein the extracellular domain does not comprise the amino acid sequence of an extracellular domain of SEQ ID NO:6.

In one embodiment, the extracellular domain is fused to a heterologous polypeptide, forming a chimeric polypeptide. In another embodiment, the extracellular domain comprises the amino acid sequence of an extracellular domain of SEQ ID NO:2 or SEQ ID NO:4.

In another aspect, the present invention provides an antibody that selectively binds to a mechanosensory transduction protein, the protein having at least one of the following characteristics: (i) comprising greater than about 70% amino acid sequence identity to SEQ ID NO:2 or SEQ ID NO:4; (ii) comprising an amino acid sequence selected from the group consisting of SEQ ID NO:7, SEQ ID NO:8, and SEQ ID NO:9; or (iii) specifically binding to polyclonal antibodies generated against a polypeptide comprising an amino acid sequence of SEQ ID NO:2, or SEQ ID NO:4; wherein the protein does not comprise the amino acid sequence of SEQ ID NO:6.

In another aspect, the present invention provides a method for identifying a compound that modulates mechanosensory receptor activity in eukaryotic cells, the method comprising the steps of: (i) contacting the compound with a mechanosensory receptor protein, the protein having at least one of the following characteristics: (a) comprising greater than about 70% amino acid sequence identity to a sequence selected from the group consisting of SEQ ID NO:2, SEQ ID NO:4, and SEQ ID NO:6; (b) comprising an amino acid sequence selected from the group consisting of SEQ ID NO:7, SEQ ID NO:8, and SEQ ID NO:9; or (c) specifically binding to polyclonal antibodies generated against a polypeptide comprising an amino acid sequence selected from the group consisting of SEQ ID NO:2, SEQ ID NO:4, and SEQ ID NO:6; and (ii) determining the functional effect of the compound on the mechanosensory receptor protein.

In one embodiment, the mechanosensory receptor protein is expressed in a eukaryotic cell or cell membrane. In another embodiment, the functional effect is determined by detecting a change in the mechanoreceptor potential of the cell or cell membrane. In another embodiment, the functional effect is determined by detecting a change in an intracellular ion concentration. In another embodiment, the ion is selected from the group consisting of $K^+$ and $Ca^{2+}$. In another embodiment, the protein comprises an amino acid sequence selected from the group consisting of SEQ ID NO:2, SEQ ID NO:4, and SEQ ID NO:6. In another embodiment, the protein is recombinant. In another embodiment, the functional effect is a physical interaction with the receptor protein.

In another aspect, the present invention provides a method of genotyping a human for a mechanosensory transduction channel locus, the method comprising detecting a mutation in a nucleic acid encoding a mechanosensory transduction channel in the human, the protein having at least one of the following characteristics: (a) comprising greater than about 70% amino acid sequence identity to a polypeptide having a sequence of SEQ ID NO:2; (b) having greater than about 90% amino acid sequence identity to a polypeptide having a sequence of SEQ ID NO:5; (c) comprising an amino acid sequence selected from the group consisting of SEQ ID NO:6, SEQ ID NO:7, and SEQ ID NO:8; or (d) specifically binding to polyclonal antibodies generated against a polypeptide selected from the group consisting of SEQ ID NO:2, SEQ ID NO:5, SEQ ID NO:6, SEQ ID NO:7, and SEQ ID NO:8; wherein the mutation introduces a premature stop codon into the nucleic acid 5' to the transmembrane domain region of the protein, or is a missense mutation removing a cysteine residue between transmembrane segments 4 and 5 of the protein.

BRIEF DESCRIPTION OF THE DRAWINGS

FIG. 1A-C shows a continuing alignment between *Drosophila melanogaster* and *Caenorhabditis elegans* MSC homologs.

DETAILED DESCRIPTION OF THE INVENTION

Introduction

The present invention provides, for the first time, nucleic acids encoding a eukaryotic mechanosensory transduction channel (MSC) protein. Mutations in these nucleic acids and the proteins they encode are responsible for the "no-mechanoreceptor potential" phenotype in *Drosophila*, a phenotype involving uncoordination, often to the point of lethality, and a loss of mechanoreceptor potential in the bristles of mutant flies (Kernan et al., *Neuron* 12:1195-1206 (1994)). The proteins encoded by these nucleic acids form channels (e.g., as tetramers) that can directly detect mechanical stimuli and convert them into electrical signals. These proteins can detect mechanical stimuli in any of a number of sensory cells, such as neuronal sensory cells, hair cells, and others. These nucleic acids and the proteins they encode can be used as probes for sensory cells in animals, and can be used to diagnose and treat any of a number of human conditions involving inherited, casual, or environmentally-induced loss of mechanosensory transduction activity.

The present invention also provides methods of screening for modulators, e.g., activators, inhibitors, enhancers, etc., of mechanosensory transduction channels. Such modulators would be useful to alter mechanosensory transduction activity in an animal, e.g., for the treatment of any of a number of human disorders. Thus, the invention provides assays for mechanosensory transduction modulation, where the MSC proteins act as a direct or indirect reporter for mechanosensory transduction activity. MSC proteins can be used in assays, in vitro, in vivo, or ex vivo, to detect changes in ion flux, ion concentration, membrane potential, signal transduction, transcription, or other biological or biophysical effects of mechanical stimulus detection.

In one embodiment, MSC proteins can be used as indirect reporters via attachment to a second reporter molecule such as green fluorescent protein (see, e.g., Mistili & Spector, *Nature Biotechnology*, 15:961-964 (1997)). In one embodiment, MSC proteins are recombinantly expressed in cells, e.g., *Xenopus* oocytes, and modulation of mechanosensory transduction is assayed by detecting changes in transmembrane potential, mechanosensory potential, intracellular ion concentration, ion flux, and the like.

In certain embodiments, potential modulators are identified by virtue of an ability to physically interact with an MSC protein. Assays for physically-interacting molecules would provide an efficient primary screen for candidate MSC modulators, and, in addition, would allow the identification of proteins and other compounds that naturally interact with MSC proteins in vivo.

The invention also provides methods of detecting MSC nucleic acid and protein expression, allowing investigation into mechanosensory regulation and the identification of mechanosensory cells. The present nucleic acids and proteins can also be used to genotype an animal, including humans, for forensic, paternity, epidemiological, or other investigations. The present invention also provides conserved sequences found in multiple MSC sequences, allowing the identification of even distantly related MSC homologs (see, for example, SEQ ID NOs:7-9). In addition, the present invention provides methods for identifying mutations in a mechanosensory transduction channel protein that eliminate or reduce function of the channel. Such mutations likely underlie one or more of the human conditions involving loss of mechanosensation discussed herein. As such, the invention provides methods of diagnosing mechanosensory transduction defects in animals.

Functionally, the MSC proteins form, within a cell membrane, a channel that directly detects mechanical stimuli and, in response to the stimuli, allows the influx of cations into a cell, thereby depolarizing the cell and initiating an electrical, i.e. neural, signal.

Structurally, the nucleotide sequences of MSCs (see, e.g., SEQ ID NOs: 1, 3, and 5, representing the *Drosophila* genomic, *Drosophila* cDNA, and *Caenorhabditis elegans* genomic sequences, respectively) encode polypeptides of from about 1619-1709 amino acids with a predicted molecular weight of about 177 kDa (see, e.g., SEQ ID NOs:2, 4, and 6). The MSC genes typically contain about 19 exons, encoding a protein with about 27 ankyrin repeats and from 6-11, typically about 8, transmembrane domains. Such proteins are weakly related to the TRP family of epithelial cation channels. MSC homologs from other species typically share at least about 70% identity over a region of at least about 25 amino acids in length, preferably 50 to 100 amino acids in length.

The present invention provides nucleic acids comprising an MSC wherein the nucleic acid is less than 120, 90, 60, 30, 20, 10, or 7 kb. In addition, nucleic acids comprising MSCs are provided wherein the MSC polynucleotide is isolated away from its genomic neighbors, i.e., the nucleic acid does not comprise any genes that are located within the same genomic region as the MSC gene.

The present invention also provides polymorphic variants of the MSC depicted in SEQ ID NO:2: variant #1, in which an isoleucine residue is substituted for a leucine residue at amino acid position 6; variant #2, in which a glycine residue is substituted for an alanine residue at amino acid position 13; and variant #3, in which an arginine residue is substituted for a lysine residue at amino acid position 22.

The present invention also provides polymorphic variants of the MSC depicted in SEQ ID NO:4: variant #1, in which an isoleucine residue is substituted for a leucine residue at amino acid position 24; variant #2, in which an alanine residue is substituted for a glycine residue at amino acid position 26; and variant #3, in which an aspartic acid residue is substituted for a glutamic acid residue at amino acid position 30.

The present invention also provides mutated MSC sequences that eliminate mechanosensory transduction activity in vivo. For example, mutations that prematurely truncate MSC proteins in the ankyrin repeat region, or missense mutations that alter a cysteine residue between transmembrane segments four and five, e.g., a C to Y substitution, have been discovered that eliminate or severely reduce MSC activity. Such mutations can be used, e.g., to detect defects in mechanosensation, specifically in mechanosensory transduction channels, in an animal such as a human.

Specific regions of MSC may be used to identify polymorphic variants, interspecies homologs, and alleles of MSC. Such identification can be made in vitro, e.g., under stringent hybridization conditions or by PCR (e.g., using primers encoding SEQ ID NOs 7-9) and sequencing, or by using the sequence information provided herein in a computer system for comparison with other nucleotide sequences. Typically, identification of polymorphic variants and alleles of MSC proteins is made by comparing an amino acid sequence of about 25 amino acids or more, e.g., 50-100 amino acids. Amino acid identify of approximately at least about 70% or above, preferably 80%, most preferably 90-95% or above typically demonstrates that a protein is a polymorphic variant, interspecies homolog, or allele of MSC protein. Sequence comparison can be performed using any of the sequence comparison algorithms discussed herein. Antibodies that specifically bind to MSC protein or a conserved region thereof can also be used to identify alleles, interspecies homologs, and polymorphic variants.

Polymorphic variants, interspecies homologs, and alleles of MSC proteins can be confirmed by examining mechanosensory cell-specific expression of the putative MSC homolog. Typically, an MSC protein having a sequence of SEQ ID NO:2, 4, or 6 can be used as a positive control in comparison to the putative homolog. Such putative homologs are expected to retain the MSC structure described herein, i.e. intracellular domain with multiple, e.g., 27, ankyrin repeats, and a transmembrane domain containing multiple, e.g, 8, transmembrane domains.

The present invention also provides promoters, enhancers, 5'- and 3'-untranslated regions, and numerous other regulatory elements that control the transcription, translation, mRNA stability, mRNA localization, and other factors regulating MSC expression. For example, SEQ ID NO:1 provides genomic DNA sequence including MSC coding sequence as well as upstream and downstream regulatory sequences, including promoter sequences, etc. Promoters and other regulatory sequences can be identified using standard methods well known to those of skill in the art, including by homology to well conserved regulatory elements such as the TATA box or other elements, as taught, e.g., in Ausubel et al., supra, or in Lewin, *Genes IV* (1990). Promoter, enhancer, and other regulatory elements can also be determined functionally, e.g., by fusing specific regions of SEQ ID NO:1 to a reporter gene and determining which regions are sufficient for expression of the reporter gene, or by mutagenizing specific regions of SEQ ID NO:1 and thereby determining which regions are required for expression. Such methods are well known to those of skill in the art. Any of the present regulatory elements can be used in isolation or together, and can be used to drive the expression of an MSC protein, a marker protein, or any protein or RNA that is desirably expressed in a cell or other expression system. In preferred embodiments, an MSC regulatory element is used to drive the expression of a protein, e.g., an MSC or a heterologous polypeptide, in a tissue-specific manner, i.e., specifically in mechanosensory cells.

MSC nucleotide and amino acid sequences can also be used to construct models of mechanosensory transduction cell proteins in a computer system. Such models can be used, e.g., to identify compounds that may interact with, activate, or inhibit MSC protein channels. Such compounds can then be used for various applications, such as to modulate mechanosensory transduction activity in vivo or to investigate the various roles of MSC in mechanosensory transduction in vivo.

The isolation of MSC protein also provides a means for assaying for inhibitors and activators of mechanosensory transduction channels, as well as for molecules, e.g., proteins, that interact with MSC proteins in vitro or in vivo. Biologically active MSC protein channels are useful for testing inhibitors and activators of MSC as mechanosensory transduction channels using in vivo and in vitro expression, e.g., in oocytes, and measuring MSC expression, phosphorylation state, membrane potential, mechanosensory potential, intra- or extra-cellular ion concentration, ion flux, and the like. Molecules can also be screened for the ability to physically interact with, e.g., bind to, MSC proteins, fragments thereof, or MSC nucleic acids, e.g., MSC promoter sequences, as shown in SEQ ID NO:1 and SEQ ID NO:3. Such interacting molecules can interact with any part of an MSC, e.g., the extracellular domain, transmembrane domain region, or intracellular domain, e.g., an ankyrin repeat. Such molecules may be involved in, or used to identify molecules capable of modulating, any aspect of MSC activity, including channel formation, detection of a mechanical stimulus, opening and/or closing of the channel, ion specificity of the channel, adaptation of the channel, or any other functional or physical aspect of the channel.

The present invention also provides assays, preferably high throughput assays, to identify molecules that interact with and/or modulate an MSC polypeptide. In numerous assays, a particular domain of an MSC is used, e.g., an extracellular, transmembrane, or intracellular domain. In numerous embodiments, an extracellular domain is bound to a solid substrate, and used, e.g., to isolate enhancers, inhibitors, or any molecule that can bind to and/or modulate the activity of an extracellular domain of an MSC polypeptide. In certain embodiments, a domain of an MSC polypeptide, e.g., an extracellular, transmembrane, or intracellular domain, is fused to a heterologous polypeptide, thereby forming a chimeric polypeptide. Such chimeric polypeptides are useful, e.g., in assays to identify modulators of an MSC polypeptide.

Such modulators and interacting molecules can be used for various purposes, such as to further investigate mechanosensory transduction channel activity in animal cells, or to modulate mechanosensory transduction activity in cells, e.g. to treat one or more conditions associated with a mechanosensory defect. It will be appreciated that in any of the binding assays or the in vitro or in vivo functional assays described herein, a full-length MSC can be used, or, alternatively, a fragment of an MSC can be used, for example a region containing only the ankyrin repeats, containing only the transmembrane domains, containing only the extracellular domain, or containing only a fragment of any these regions, will be used. Further, such fragments can be used alone, or fused to a heterologous protein any other molecule.

Definitions

The term "mechanosensory transduction protein" refers to a polypeptide that, when expressed in a cell or an oocyte, confers onto the cell an ability to detect changes in pressure, motion, or any other mechanical stimulus as described herein. Such proteins can be expressed naturally or recombinantly, and can confer such activity on the cell in vitro, in vivo, or ex vivo. Typically, such proteins will be at least about 70% identical to an amino acid sequence of SEQ ID NO:2, 4, or 6, and will include intracellular domains, including ankyrin repeats, and transmembrane domains. However, such proteins can also refer to one or more domains of these sequences in isolation, e.g., the ankyrin repeats, the extracellular domain, the transmembrane domains, or any subfragments thereof, alone. Such proteins can be involved in any mechanosensory process, such as tactile sensation, proprioception, hearing, baroreception, and others.

The term "MSC protein" refers to polymorphic variants, alleles, mutants, and interspecies homologs that: (1) have about 70% amino acid sequence identity, preferably about 85-90% amino acid sequence identity to SEQ ID NOS:2, 4, or 6 over a window of about 25 amino acids, preferably 50-100 amino acids; (2) bind to antibodies raised against an immunogen comprising an amino acid sequence selected from the group consisting of SEQ ID NO:2, 4, 6-9, and conservatively modified variants thereof; (3) specifically hybridize (with a size of at least about 500, preferably at least about 900 nucleotides) under stringent hybridization and/or wash conditions to a sequence selected from the group consisting of SEQ ID NO:1, 3, and 5, and conservatively modified variants thereof; or (4) are amplified by primers that specifically hybridize under stringent hybridization conditions to the same sequence as a degenerate primer sets encoding SEQ ID NOS: 7-9.

"Biological sample" as used herein is a sample of biological tissue or fluid that contains an MSC protein or nucleic acid encoding an MSC protein. Such samples include, but are not limited to, tissue isolated from humans, mice, rats, and other animals. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues include tissues involved in mechanosensation, such as the inner ear or any mechanosensory epithelial or neural tissue.

The phrase "functional effects" in the context of assays for testing compounds that modulate MSC protein-mediated mechanosensory transduction includes the determination of any parameter that is indirectly or directly under the influence of the channel. It includes changes in ion flux, membrane potential, current flow, transcription, MSC protein phosphorylation or dephosphorylation, signal transduction, in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of MSC proteins. Such functional effects can be measured by any means known to those skilled in the art, e.g., patch clamping, voltage-sensitive dyes, whole-cell currents, radioisotope efflux, inducible markers, oocyte MSC expression; tissue culture cell MSC expression; transcriptional activation of MSC protein; ligand-binding assays; membrane potential and conductance changes; ion-flux assays; changes in intracellular calcium levels; neurotransmitter release, and the like.

A "physical effect" in the context of assays for testing the ability of a compound to affect the activity of or bind to an MSC polypeptide refers to any detectable alteration in the physical property or behavior of an MSC polypeptide due to an interaction with a heterologous compound, or any detection of a physical interaction using, e.g., electrophoretic, chromatographic, or immunologically-based assay, or using a two-hybrid screen as described infra. For example, a physical effect can include any alteration in any biophysical property of an MSC channel comprising an MSC polypeptide, e.g., the cation specificity or mechanical sensitivity of the channel, or any structural or biochemical properties of an MSC polypeptide, e.g., its secondary, tertiary, or quaternary structure, hydrodynamic properties, spectral properties, chemical properties, or any other such property as described, e.g., in Creighton, *Proteins* (1984).

"Inhibitors," "activators," and "modulators" of MSC refer to any inhibitory or activating molecules identified using in vitro and in vivo assays for mechanosensory transduction, e.g., agonists, antagonists, and their homologs and mimetics. Inhibitors are compounds that decrease, block, prevent, delay activation, inactivate, desensitize, or down regulate mechanosensory transduction, e.g., antagonists. Activators are compounds that increase, open, activate, facilitate, enhance activation, sensitize or up-regulate mechanosensory transduction, e.g., agonists. Modulators include genetically-modified versions of MSC, e.g., with altered activity, as well as naturally-occurring and synthetic ligands, antagonists, agonists, small chemical molecules and the like. Such assays for inhibitors and activators include, e.g., expressing MSC protein in cells or cell membranes, applying putative modulator compounds, and then determining the functional effects on mechanosensory transduction, as described above. Samples or assays comprising MSC that are treated with a potential activator, inhibitor, or modulator are compared to control samples without the inhibitor, activator, or modulator to examine the extent of inhibition. Control samples (untreated with inhibitors) are assigned a relative MSC activity value of 100%. Inhibition of MSC is achieved when the C activity value relative to the control is about 80%, preferably 50%, more preferably 25-1%. Activation of MSCs is achieved when the MSC activity value relative to the control is 110%, more preferably 150%, more preferably 200-500%, more preferably 1000-3000% higher.

"Biologically active" MSC refers to an MSC protein, or a nucleic acid encoding the MSC protein, having mechanosensory transduction activity as described above, involved in mechanosensory transduction in mechanosensory cells.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high-performance liquid chromatography. A protein that is the predominant species present in a preparation is substantially purified. In particular, an isolated MSC nucleic acid is separated, e.g., from open reading frames or fragments of open reading frames, e.g., that naturally flank the MSC gene and encode proteins other than MSC protein. An isolated MSC nucleic acid is typically contiguous, i.e., heterologous sequences are typically not embedded in the MSC nucleic acid sequence, although heterologous sequences are often found ajoining an isolated MSC nucleic acid sequence. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions)

and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group., e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes (A, T, G, C, U, etc.).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the any position of one or more selected (or all) codons is substituted with mixed-base and/or deoxyinosine residues to yield a codon encoding the same amino acid residue (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, *Proteins* (1984) for a discussion of amino acid properties).

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein, a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions," or "stringent wash conditions," refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Washes can be performed for varying amounts of time, e.g., 5 minutes, 15 minutes, 30 minutes, 1 hour or more. Exemplary stringent hybridization or wash conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions," or "moderately stringent wash conditions," include a hybridization in a buffer of 40% formamide, 1 M NaCl, 1% SDS at 37° C., and a wash in 1×SSC at 45° C. Washes can be performed for varying amounts of time, e.g., 5 minutes, 15 minutes, 30 minutes, 1 hour or more. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization and/or wash conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

"Antibody" refers to a polypeptide substantially encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-MSC" antibody is an antibody or antibody fragment that specifically binds a polypeptide encoded by the MSC gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to MSC protein from specific species such as rat, mouse, or human can be selected to obtain only those polyclonal antibodies that are specifically immunoreactive with MSC and not with other proteins, except for polymorphic variants and alleles of MSC. This selection may be achieved by subtracting out antibodies that cross-react with MSC proteins from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

Isolation of MSC Nucleic Acids

General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

Cloning MSC Nucleic Acids

In general, the nucleic acid sequences encoding MSC and related nucleic acid sequence homologs are cloned from cDNA and genomic DNA libraries by hybridization with a probe, or isolated using amplification techniques with oligonucleotide primers. For example, MSC sequences are typically isolated from mammalian nucleic acid (genomic or cDNA) libraries by hybridizing with a nucleic acid probe, the sequence of which can be derived from SEQ ID NOS:1, 3, or 5. MSC RNA and cDNA can be isolated from any of a number of tissues, such as hair cells of the inner ear, sensory neurons, or any other mechanosensory cell.

Amplification techniques using primers can also be used to amplify and isolate an MSC polynucleotide from DNA or RNA. The degenerate primers encoding the following amino acid sequences can also be used to amplify a sequence of MSC: SEQ ID NOS:7-9 (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length MSC sequences.

Nucleic acids encoding MSC proteins can also be isolated from expression libraries using antibodies as probes. Such polyclonal or monoclonal antibodies can be raised using polypeptides comprising the sequence of, e.g., SEQ ID NOS: 2, 4, 6, 7, 8 or 9.

cDNA and Genomic Libraries

MSC polymorphic variants, alleles, and interspecies homologs that are substantially identical to MSC proteins can be isolated using MSC nucleic acid probes, and oligonucleotides under stringent hybridization conditions, by screening libraries. Alternatively, expression libraries can be used to clone MSC and MSC polymorphic variants, alleles, and interspecies homologs, by detecting expressed homologs immunologically with antisera or purified antibodies made against MSC, which also recognize and selectively bind to the MSC homolog.

To make a cDNA library, one should choose a source that is rich in MSC mRNA, e.g., inner ear tissue or other sources of mechanosensory cells, e.g., sensory epithelial cells or neurons. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

Amplification Methods

An alternative method of isolating MSC nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of MSC directly from mRNA, from cDNA, from genomic libraries or cDNA libraries. Degenerate oligonucleotides can be designed to amplify MSC homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of MSC-encoding mRNA in physiological samples, for nucleic acid sequencing, or for other purposes. Genes amplified by the PCR reaction can be purified from agarose gels and cloned into an appropriate vector.

Gene expression of MSC protein can be analyzed by techniques known in the art, e.g., reverse transcription and amplification of mRNA, isolation of total RNA or poly $A^+$ RNA, Northern blotting, dot blotting, in situ hybridization, RNase protection, probing DNA microchip arrays, and the like. In one embodiment, high density oligonucleotide analysis technology (e.g., GeneChip™) is used to identify homologs and polymorphic variants of MSC. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

Synthetic oligonucleotides can be used to construct recombinant MSC genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the MSC nucleic acid. The specific subsequence is then ligated into an expression vector.

The nucleic acid encoding the MSC protein is typically cloned into intermediate vectors before transformation into prokaryotic or eukaryotic cells for replication and/or expression. These intermediate vectors are typically prokaryote vectors, e.g., plasmids, or shuttle vectors.

Expressing Nucleic Acids in Prokaryotes and Eukaryotes
Expression Vectors

To obtain high level expression of a cloned gene or nucleic acid, such as those cDNAs encoding an MSC protein, one typically subclones MSC into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the MSC protein are available in, e.g., *E. coli, Bacillus* sp., and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available.

Promoters

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the MSC-encoding nucleic acid in host cells. A typical expression cassette thus contains a promoter operably linked to the nucleic acid sequence encoding MSC protein and signals required for efficient polyadenylation of the transcript, ribosome binding sites, and translation termination. The nucleic acid sequence encoding MSC protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Other Elements

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a MSC encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Transfection Methods

Standard transfection methods are used to produce bacterial, mammalian, yeast or insect cell lines that express large quantities of MSC protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing MSC.

After the expression vector is introduced into the cells, the transfected cells are cultured under conditions favoring expression of MSC, which is recovered from the culture using standard techniques identified below.

Purification of MSC Proteins

Either naturally occurring or recombinant MSC protein can be purified for use in functional assays. Preferably, recombinant MSC is purified. Naturally occurring MSC is purified, e.g., from mammalian tissue such as inner ear tissue or other tissues including mechanosensory cells. Recombinant MSC is purified from any suitable expression system.

MSC protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant MSC is being purified. For example, proteins having established molecular adhesion properties can be reversibly fused to MSC. With the appropriate ligand, MSC can be selectively adsorbed to a purification column and then freed from the column in a relatively pure form. The fused protein is then removed by enzymatic activity. Finally MSC could be purified using immunoaffinity columns.

Purification from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of MSC inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. MSC is separated from other bacterial proteins by standard separation techniques, e.g., with Ni-NTA agarose resin.

Alternatively, it is possible to purify MSC protein from bacteria periplasm. After lysis of the bacteria, when MSC is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Purification Techniques

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of MSC protein can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

MSC proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Affinity-Based Techniques

Any of a number of affinity based techniques can be used to isolate MSC proteins from cells, cell extracts, or other sources. For example, affinity columns can be made using anti-MSC antibodies or other MSC-binding proteins, or physically-interacting proteins can be identified by co-immunoprecipitation or other methods. Such methods are well known to those of skill in the art and are taught, e.g., in Ausubel et al., Sambrook et al., Harlow and Lane, all supra.

Immunological Detection

In addition to the detection of MS genes and gene expression using nucleic acid hybridization technology, one can also use immunoassays to detect MSC proteins, e.g., to identify mechanosensory cells and variants of MSC proteins. Immunoassays can be used to qualitatively or quantitatively analyze MSC proteins. A general overview of the applicable technology can be found in Harlow & Lane, *Antibodies: A Laboratory Manual* (1988).

Antibodies to MSC Proteins

Methods of producing polyclonal and monoclonal antibodies that react specifically with MSC proteins are known to those of skill in the art (see, e.g., Coligan, *Current Protocols in Immunology* (1991); Harlow & Lane, supra; Goding, Monoclonal *Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of MSC peptides or a full-length protein may be used to produce antibodies specifically reactive with MSC protein. For example, recombinant MSC protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to MSC proteins. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-MSC proteins or even other related proteins from other organisms, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

Once MSC specific antibodies are available, MSC proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

Immunological Binding Assays

MSC proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the MSC protein or antigenic subsequence thereof). The antibody (e.g., anti-MSC) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled MSC polypeptide or a labeled anti-MSC antibody. Alternatively, the labeling agent may be a third moiety, such a secondary antibody, that specifically binds to the antibody/MSC complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 11° C. to 40° C.

Non-Competitive Formats

Immunoassays for detecting MSC proteins in samples may be either competitive or noncompetitive. Noncompetitive immunoassays are assays in which the amount of antigen is directly measured. In one preferred "sandwich" assay, for example, the anti-MSC antibodies can be bound directly to a solid substrate on which they are immobilized. These immobilized antibodies then capture MSC proteins present in the test sample. The MSC protein is thus immobilized and then bound by a labeling agent, such as a second MSC antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Formats

In competitive assays, the amount of MSC proteins present in the sample is measured indirectly by measuring the amount of a known, added (exogenous) MSC proteins displaced (competed away) from an anti-MSC antibody by the unknown MSC protein present in a sample. In one competitive assay, a known amount of MSC protein is added to a sample and the sample is then contacted with an antibody that specifically binds to MSC proteins. The amount of exogenous MSC protein bound to the antibody is inversely proportional to the concentration of MSC protein present in the sample. In a particularly preferred embodiment, the antibody is immobilized on a solid substrate. The amount of MSC protein bound to the antibody may be determined either by measuring the amount of MSC protein present in a MSC protein/antibody complex, or alternatively by measuring the amount of remaining uncomplexed protein. The amount of MSC protein may be detected by providing a labeled MSC protein molecule.

A hapten inhibition assay is another preferred competitive assay. In this assay the known MSC protein, is immobilized on a solid substrate. A known amount of anti-MSC antibody is added to the sample, and the sample is then contacted with the immobilized MSC protein. The amount of anti-MSC antibody bound to the known immobilized MSC protein is inversely proportional to the amount of MSC protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determination

Immunoassays in the competitive binding format can also be used for crossreactivity determinations. For example, a protein at least partially encoded by SEQ ID NOS:1, 3, or 5 can be immobilized to a solid support. Proteins (e.g., MSC proteins and homologs) are added to the assay that compete for binding of the antisera to the immobilized antigen. The ability of the added proteins to compete for binding of the antisera to the immobilized protein is compared to the ability of MSC protein encoded by SEQ ID NO:1, 3, or 5 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. In one embodiment, antibodies that crossreact with MSC proteins from a different species are selectively removed, thereby enhancing the species-specificity of the antisera. For example, to obtain antibodies that specifically react with *Drosophila* MSC, the ability of SEQ ID NO:4 and SEQ ID NO:6 to compete for binding to antisera directed against SEQ ID NO:4 are compared, and antibodies that cross-react with SEQ ID NO:6 selectively removed.

The immunoabsorbed and pooled antisera are then used in a competitive binding immunoassay as described above to compare a second protein, thought to be perhaps an allele or polymorphic variant of MSC protein, to the immunogen protein (i.e., MSC protein of SEQ ID NOS:2, 4, 6-9). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS:1, 3, or 5 that is required to inhibit 50% of binding, then the second protein is said to specifically bind to the polyclonal antibodies generated to an MSC protein immunogen.

Other Formats

Western blot (immunoblot) analysis is used to detect and quantify the presence of MSC protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind MSC protein. The anti-MSC antibodies specifically bind to the MSC protein on the solid support. These antibodies may be directly labeled or alternatively may be subsequently detected using labeled antibodies (e.g., labeled sheep anti-mouse antibodies) that specifically bind to the anti-MSC antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly where the assay involves an antigen or antibody immobilized on a solid substrate, it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used, with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize MSC protein, or secondary antibodies that recognize anti-MSC protein.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Modulators of Mechanosensory Transduction

In numerous embodiments of this invention, assays will be performed to detect compounds that affect mechanosensory transduction in a cell. Such assays can involve the identification of compounds that interact with MSC proteins, either physically or genetically, and can thus rely on any of a number of standard methods to detect physical or genetic interactions between compounds. Such assays can also involve the detection of mechanosensory transduction in a cell or cell membrane, either in vitro or in vivo, and can thus involve the detection of transduction activity in the cell through any standard assay, e.g., by measuring ion flux, changes in membrane potential, and the like. Such cell-based assays can be performed in any type of cell, e.g., a sensory cell that naturally expresses MSC, a cultured cell that produces MSC due to recombinant expression, or, preferably, an oocyte that is induced to produce MSC through any of a number of means, as described infra.

In any of the binding or functional assays described herein, in vivo or in vitro, any MSC protein, or any derivative, variation, homolog, or fragment of an MSC protein, can be used. Preferably, the MSC protein is at least about 70% identical to SEQ ID NO:2, 4, or 6, and/or comprises SEQ ID NO:7, 8, or 9. In numerous embodiments, a fragment of an MSC protein is used. For example, a fragment that contains only the extracellular region, the ankyrin repeat region, or the transmembrane domains, i.e. the channel region (see, e.g., SEQ ID NOs:10-17), can be used. Such fragments can be used alone, in combination with other MSC fragments, or in combination with sequences from a heterologous protein, e.g., the fragments can be fused to a heterologous polypeptide, thereby forming a chimeric polypeptide. Any individual domain or sequence, however small, can readily be used in the present invention, e.g., a single ankyrin repeat, transmembrane domain, etc., alone or in combination with other domains or with sequences from heterologous proteins. Such fragments and isolated domains of MSC proteins comprise an essential aspect of the present invention, and are of substantial importance in the assays described herein.

Assays for MSC-Interacting Compounds

In certain embodiments, assays will be performed to identify molecules that physically or genetically interact with MSC proteins. Such molecules can be any type of molecule, including polypeptides, polynucleotides, amino acids, nucleotides, carbohydrates, lipids, or any other organic or inorganic molecule. Such molecules may represent molecules that normally interact with MSC to effect mechanosensation in sensory cells, or may be synthetic or other molecules that are capable of interacting with MSC and which can potentially be used to modulate MSC activity in cells, or used as lead compounds to identify classes of molecules that can interact with and/or modulate MSC. Such assays may represent physical binding assays, such as affinity chromatography, immunoprecipitation, two-hybrid screens, or other binding assays, or may represent genetic assays as described infra.

Such interacting molecules may interact with any part of an MSC protein, e.g., the extracellular domain, the transmembrane domain region, or the intracellular domain, including the ankyrin repeats. MSC proteins act in sensory cells to depolarize the cell in response to a mechanical input outside of the cell. As such, interacting molecules may include those that interact with the extracellular domain of the protein, and which may enhance, inhibit, or otherwise modulate the detection of a mechanical input, and which may be part of, or interact with, an extracellular structure involved in mechanical detection, such as the stereocilium of a hair cell. An interacting molecule may also interact with the transmembrane domain region of the protein, and may be involved in, or capable of modulating, the formation of a channel, the opening or closing of a channel, etc. In addition, an interacting molecule may interact with an intracellular part of a channel, e.g., an ankyrin repeat, and be involved in, e.g., the function, regulation, adaptation, or any other aspect of channel activity.

The MSC protein used in such assays can be a full-length MSC protein or any subdomain of an MSC protein. In preferred embodiments, a fragment of an MSC protein comprising an extracellular domain of an MSC will be used. Molecules that bind to the extracellular domain of an MSC are particularly useful for the identification of modulators of MSC activity, as they are typically soluble and readily included in high throughput screening assay formats, as described infra.

Assays for Physical Interactions

Compounds that interact with MSC proteins can be isolated based on an ability to specifically bind to an MSC protein or fragment thereof. In numerous embodiments, the MSC protein or protein fragment will be attached to a solid support. In one embodiment, affinity columns are made using the MSC polypeptide, and physically-interacting molecules are identified. It will be apparent to one of skill that chromatographic techniques can be performed at any scale and using equipment from many different manufacturers (e.g., Pharmacia Biotech). In addition, molecules that interact with MSC proteins in vivo can be identified by co-immunoprecipitation or other methods, i.e. immunoprecipitating MSC proteins using anti-MSC antibodies from a cell or cell extract, and identifying compounds, e.g., proteins, that are precipitated along with the MSC protein. Such methods are well known to those of skill in the art and are taught, e.g., in Ausubel et al., Sambrook et al., Harlow & Lane, all supra.

Two-hybrid screens can also be used to identify polypeptides that interact in vivo with an MSC or a fragment thereof (Fields et al., Nature 340:245-246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, which can be detected using standard methods. In the present invention, an MSC polypeptide is fused to one of the two domains of the transcription factor, and the potential MSC-binding polypeptides (e.g., encoded by a cDNA library) are fused to the other domain. Such methods are well known to those of skill in the art, and are taught, e.g., in Ausubel et al., supra.

Assays for Genetic Interactions

It is expected that MSCs are assembled into multi-protein complexes in which the interactions are mediated by the large number of ankyrin repeats found in the N terminus of the protein. Genetic screens can thus be performed to identify such additional proteins that are involved in the transduction pathway. For example, genetic strains are produced that possess only a partially functional nompC (MSC) gene, which confers an incomplete mechanical sensitivity to the fly. Ideally, a vial of these flies would produce only 10-20 viable homozygotes. In this sensitized genetic background, flies will be screened for mutations in other genes that either suppress or enhance the survival of the mutant flies. Flies will be mutagenized using any standard chemical, radiation-based, or genetic method and then crossed into the above-described sensitized genetic background, followed by counting the number of homozygous progeny. Mutations that produce more than 10-20 flies per vial are considered suppressors of nompC, and those that produce fewer flies are considered enhancers. Similar screens can be performed using MSC genes in genetically tractable mammals, e.g., mice.

Assays for MSC Activity

The activity of MSC polypeptides, and any homolog, variant, derivative, or fragment thereof can be assessed using a variety of in vitro and in vivo assays for mechanoreceptor potential, e.g., measuring current, measuring membrane potential, measuring ion flux, e.g., potassium or calcium, measuring transcription levels, measuring neurotransmitter levels, using e.g., voltage-sensitive dyes, radioactive tracers, patch-clamp electrophysiology, transcription assays, and the like. Furthermore, such assays can be used to test for modulators, e.g., inhibitors or activators, of MSC. Such modulators can be a protein, amino acid, nucleic acid, nucleotide, lipid, carbohydrate, or any type of organic or inorganic molecule, including genetically altered versions of MSC proteins. Such assays can be performed using any of a large number of cells, including oocytes, cultured cells, sensory epithelial or neural cells, and others, and can be present in vitro or in vivo. Such cells can contain naturally expressed MSC, can be induced to express MSC using recombinant or other methods, or can comprise MSC by direct addition of the protein to the cell or cell membrane. In numerous embodiments, the cell or cell membrane comprising the MSC polypeptide will be anchored to a solid support.

Preferably, the MSC proteins used in the assay is selected from a polypeptide having a sequence of SEQ ID NOS:2, 4, or 6, or a conservatively modified variant thereof. Alternatively, the MSC protein used in the assay will be derived from a eukaryote and include an amino acid subsequence having amino acid sequence identity SEQ ID NOS:2, 4, or 6. Generally, the amino acid sequence identity will be at least 70%, preferably at least 85%, most preferably at least 90-95%. In preferred embodiments, a polypeptide comprising an extracellular domain is used, e.g., an extracellular domain of SEQ ID NO:2, 4, or 6. In such embodiments, the extracellular domain is often fused to a heterologous polypeptide, forming a chimeric polypeptide. Typically, such chimeric polypeptides will comprise an extracellular domain as well as multiple transmembrane domains, and will have mechanosensory transduction activity.

Detecting Mechanosensory Transduction

In numerous embodiments of the present invention, assays will be performed to detect alterations in an MSC protein, e.g., one expressed in a cell or cell membrane, or in mechanosensory transduction, or mechanoreceptor potential, in a cell or cell membrane, e.g., as a result of a mutation in an MSC or due to the presence of an MSC-modulating compound. Mechanosensory transduction or mechanoreceptor potential can be detected in any of a number of ways, including by detecting changes in ion flux, changes in polarization of a cell or cell membrane, changes in current, and other methods, including by measuring downstream cellular effects, e.g., neuronal signaling.

Changes in ion flux may be assessed by determining changes in polarization (i.e., electrical potential) of the cell or membrane expressing MSC. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see, e.g., Hamil et al., *PFlugers. Archiv.* 391:85 (1981). Other known assays include: radioactive ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane Biology* 137:59-70 (1994)). Generally, candidate compounds are tested in the range from 1 pM to 100 mM.

The effects of the test compounds, or sequence variation, upon the function of the MSC polypeptides can be measured by examining any of the parameters described above. In addition, any suitable physiological change that affects MSC activity, or reflects MSC activity, can be used to assess the influence of a test compound or sequence alteration on the MSC polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and other effects.

Preferred assays for mechanosensory transduction channels include cells, e.g., oocytes, that are loaded with ion or voltage sensitive dyes to report receptor activity. Assays for determining activity of such receptors can also use known agonists and antagonists for other cation channels as negative or positive controls to assess activity of tested compounds. In assays for identifying modulatory compounds (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed are those disclosed in the Molecular Probes 1997 Catalog. In addition, changes in cytoplasmic calcium, potassium, or other ion levels can be used to assess MSC function.

In vivo Assays

In certain embodiments, the mechanosensory activity of a cell will be examined in vivo. Such embodiments are useful for, e.g., examining the activity of an MSC or an MSC mutant, derivative, homolog, fragment, etc. Also, such assays are useful for detecting the activity of candidate MSC modulator in vivo. Potential MSCs can be produced in transgenic flies carrying the candidate cDNA driven by a suitable, e.g. a nompC, promoter/enhancer construct. These candidate channels can be expressed in mechanosensory neurons of flies and their mechanoelectrical activity measured with bristle recordings. Methods of producing transgenic flies and methods of detecting mechanosensory transduction activity in fly mechanosensory neurons are well known to those of skill in the art and are described, e.g., in *Drosophila*, a Practical Approach (Roberts, ed. 1986)), and in Kernan et al. (1994), respectively.

Alternatively, it is possible to screen for molecules that can mimic NOMPC activity by performing the screen in a nompC mutant background. Those molecules that rescue the mutant phenotype can be considered potential MSCs.

Assays Using Oocytes or Cultured Cells in vitro

*Xenopus* oocytes

In preferred embodiments, MSC proteins are expressed in oocytes of the frog *Xenopus laevis*, and the mechanosensory transduction of the oocyte measured. Such assays are useful, e.g., to measure the activity of homologs, variants, derivatives, and fragments of MSC proteins, as well as to measure the effect of candidate modulators on the activity of MSC protein channels in the oocytes. In such embodiments, mRNA encoding the MSC protein, or candidate MSC protein, is typically microinjected into the oocyte where it is translated. The MSC protein, and in some cases the candidate MSC, then forms a functional mechanosensory transduction channel in the oocyte which can be studied using the methods described herein. In such embodiments, MSC cDNAs are typically subcloned into specialized transcription vectors in which the cDNA insert is flanked by *Xenopus* hemoglobin 5' and 3' untranslated regions. Transcripts are made from both the sense and antisense strand of the plasmid and then polyadenylated using standard techniques. These transcripts are then microinjected into *Xenopus laeves* oocytes. After allowing a sufficient time for translation, the oocytes are subjected to voltage-clamp recording. Cell-attached patches of oocyte membrane are assayed for the presence of conductances provoked by the application of mechanical force to the membrane, e.g., using small, calibrated pressure and vacuum steps applied through the patch pipette. Because *Xenopus* oocyte membranes contain an endogenous mechanically gated conductance, which is typically observed using these methods, the conductance due to the heterologous MSC channel represents any additional conductance, i.e., beyond the background level, seen during a mechanical stimulus. In such assays, it is important to compare the sense- to the antisense- and mock-injected controls for the presence of mechanically gated conductances.

Cultured Cells

In certain embodiments, MSC proteins are expressed in cultured cells, e.g., mammalian cells, and the mechanosensory transduction activity of the cell determined. In such assays, cDNAs encoding known or candidate MSC proteins are typically subcloned into commercially available cell expression vectors, e.g., mammalian cell expression vectors, and then transfected into cultured cells. Expression vectors, transfection, and maintenance of animal cells are well known to those of skill and are taught, e.g., in Ausubel et al., supra, and Freshney, *The Culture of Animal Cells* (1993).

Cultured animal cells expressing MSC proteins, like the above-described oocytes, are subjected to cell-attached patch voltage-clamp recording during the application of mechanical stimuli such as small, calibrated pressure and suction stimuli to the patch. Osmotic membrane stress can also serve as a mechanical stimulus. Again, as eukaryotic cells generally contain endogenous mechanically gated ion channels, it is important to compare the transduction levels in the transfected cells to those in the mock-transfected controls. Any mechanically-gated conductance detectable above the level of the endogenous conductance is due to the candidate channel.

Alternatively, because MSC channels conduct calcium ions, transfected cells are loaded with a fluorescent $Ca^{2+}$ indicator dye and then stimulated with hypo- and hyper-osmotic solutions while monitoring the cell's fluorescence. Hyper- and hypo-osmotic solutions create membrane stresses that open mechanically gated ion channels. In such assays, the influx of $Ca^{2+}$ causes an increase in fluorescence of the $Ca^{2+}$ indicator dye. As with the voltage-clamp recording, it is important to compare the transfected and mock-transfected controls. Any increased fluorescence in the transfected cells during the stimuli compared to that observed in mock transfected cells is due to the presence of the MSC channel.

Biophysical Properties of MSC Channels

The effect of a sequence alteration in an MSC channel, or of a candidate modulator on a channel, can also be assessed by examining the effect of the sequence alteration or the compound on one or more structural or biophysical properties that are typical of MSC channels. For example, MSC channels show very little voltage dependence, and are instead gated by mechanical stimuli. Further, MSC channels have a non-specific cationic preference, i.e., they conduct many different cations, including some large organic cations like tetramethyl ammonium ion (although weakly). The solution bathing these channels in the *Drosophila* bristle and in vertebrate hearing organs has a high potassium ion concentration (over 100 mM), which is very unusual for an extracellular fluid. Because of this, the principal current-carrying ion in vivo is $K^+$, with a small portion of the current carried by $Ca^{2+}$. In addition, as MSC channels are completely blocked in vivo by tetraethyl ammonium ions, it is expected that the channels are also refractory to tetraethyl ammonium ions in heterologous systems. Further, MSC proteins are in general refractory to $Gd^{3+}$ ions, albeit at millimolar concentrations; in our bristle recording system, however, fly mechanoreceptor neurons are unaffected by $Gd^{3+}$ treatment.

It will be appreciated that any of these characteristics, which are typical of mechanosensory transduction channels in vivo, can be assessed in cell-attached patches in either oocytes or cultured cells to assess the effect of any potential modulator, mutation, or treatment upon an MSC protein.

Candidate Modulators and MSC-Binding Compounds

Using the present methods, any protein, amino acid, nucleic acid, nucleotide, carbohydrate, lipid, or any other organic or inorganic molecule can be assessed for its ability to bind to or modulate the activity of an MSC polypeptide. Such candidate modulators or binding proteins can be deliberately designed, e.g., a putative dominant-negative form of an MSC polypeptide or a compound predicted to bind based on a computer-based structural analysis of the protein, or can be identified using high efficiency assays to rapidly screen a large number of potential compounds, e.g., from a library of nucleic acids or a combinatorial peptide or chemical library.

Proteins

Any of a number of polypeptides can be used in the present assays to determine their ability to bind to or modulate mechanosensory transduction activity in an MSC-protein expressing cell. Such polypeptides can represent, e.g., a candidate protein or collection of proteins encoded by a library of nucleic acids, can represent a putative dominant negative form or other variant of an MSC polypeptide, can represent a collection of peptide sequences, e.g., from a combinatorial peptide library, or can be predicted using a computer-based structural analysis program.

Heterologous Proteins

Polypeptide modulators of MSC proteins can be identified using a fluorescence-based screening strategy. In such approaches, cells are first induced to stably express an MSC protein, and then transfected with a cDNA clone of interest, e.g., representing a deliberately-selected candidate modulator or a collection of random clones such as a cDNA library isolated from a sensory tissue. The transfected cells are then loaded with fluorescent $Ca^{2+}$-indicator dyes and subjected to an osmotic stimulus or a mild mechanical treatment. Heterologous proteins that exert a modulatory effect on the MSC channel will cause the cell to exhibit either an increase or a decrease in the fluorescence during the stimulus compared to a cell expressing the MSC protein alone.

MSC Protein Fragments. e.g. Dominant Negative Forms

Because MSCs are thought be part of a multi-protein complex in vivo, it is expected that a dominant-negative form of MSC can be produced by designing an MSC that lacks mechanosensory transduction activity but which can nevertheless interact in vivo with other molecules involved in mechanosensory transduction. A "dominant-negative" MSC refers to any MSC whose presence reduces mechanosensory activity in vivo, even in the presence of fully functional MSC protein. For example, overexpression of the ankyrin repeats alone (which are thought to facilitate protein-protein interactions), or in combination with a defective channel domain, will likely lead to the disruption of mechanical signaling. Alternatively, if these channels are comprised of several homomeric subunits (e.g., single MSC polypeptide units), expression of the channel moiety alone will reduce mechanosensory signaling in a dominant fashion.

In addition, because MSCs are weakly similar at a structural level to many voltage-activated channels, they could potentially contain an endogenous "ball and chain" inactivator of the channel (see, e.g., Antz et al., *Nat Struct Biol* 6(2):146-50 (1999)). Accordingly, one can potentially identify such endogenous modulators by producing small fragments of MSC, e.g., using a bacterial expression system, and assaying their ability to inhibit MSC protein activity in an assay as discussed supra.

Small Molecules

In numerous embodiments of this invention, test compounds will be small chemical molecules or peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St.

Louis, Mo.), Aldrich (St. Louis, Mo.), Sigma-Aldrich (St. Louis, Mo.), Fluka Chemika-Biochemica Analytika (Buchs Switzerland) and the like.

Combinatorial Libraries

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

High Throughput Screening

In one embodiment, the invention provides solid phase based in vitro assays in a high throughput format, where the cell, cell membrane, or tissue comprising the MSC protein is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds is possible using the integrated systems of the invention. More recently, microfluidic approaches to reagent manipulation have been developed.

Computer-Based Assays

Yet another assay for compounds that modulate MSC activity involves computer assisted drug design, in which a computer system is used to generate a three-dimensional structure of MSC proteins based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind heterologous molecules. These regions are then used to identify molecules that bind to the protein.

The three-dimensional structural model of the protein is generated by entering protein amino acid sequences of at least 10 amino acid residues or corresponding nucleic acid sequences encoding a MSC polypeptide into the computer system. For example, the amino acid sequence of the polypeptide is selected from the group consisting of SEQ ID NOS:2, 4, and 6, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD-ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential binding regions are identified by the computer system. Three-dimensional structures for potential binding molecules are generated by entering amino acid or nucleotide sequences or chemical formulas of compounds, as described above. The three-dimensional structure of the potential binding molecule is then compared to that of the MSC protein to identify molecules that bind to MSC. Binding affinity between the protein and binding molecule is determined using energy terms to determine which molecules have an enhanced probability of binding to the protein.

Computer systems are also used to screen for mutations, polymorphic variants, alleles and interspecies homologs of MSC genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated MSC protein encoding genes involves receiving input of a first nucleic acid or amino acid sequence encoding MSC proteins, e.g., a sequence selected from the group consisting of SEQ ID NOS:1-9, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in MSC protein encoding genes, and mutations associated with disease states and genetic traits.

MSC Genotyping

The present invention also provides methods to genotype an animal, including a human, for an MSC gene or protein. Typically, such genotyping involves a determination of the particular sequence, allele, or isoform of an MSC gene or protein, using any standard technique as described herein, including DNA sequencing, amplification-based, restriction enzyme-based, electrophoretic and hybridization based assays to detect variations in genomic DNA or mRNA, or immunoassays and electrophoretic assays to detect protein variations. The detection of particular alleles, sequence variations, isoforms, etc., is useful for many applications, including for forensic, paternity, epidemiological, or other investigations.

In addition, the detection of certain alleles or protein forms is useful for the detection of a mutation in an MSC gene in an animal, and is thus useful for the diagnosis of mechanosensory transduction channel defects in the animal. Such mechanosensory defects may underlie any of a large variety of conditions in animals, including conditions associated with impaired hearing, touch sensitivity, proprioception, balance, and other processes. In addition, mechanosensory defects may be associated with a loss of contact-inhibition in cells, and thus may be associated with cancer in the animal.

In particular, it has been discovered that mutations that introduce a premature stop codon into an MSC gene within the ankyrin repeat region, or mutations that remove or substitute a conserved cysteine residue between transmembrane segments 4 and 5 of the protein, result in a dramatic decrease in MSC activity and are thus useful markers for such analyses.

Pharmaceutical Compositions and Administration

Mechanosensory transduction modulators can be administered directly to the mammalian subject for modulation of mechanosensation in vivo. Administration is by any of the routes normally used for introducing a modulator compound into ultimate contact with the tissue to be treated, such as the inner ear or other mechanosensory tissue. The mechanosensory modulators are administered in any suitable manner, preferably with pharmaceutically acceptable carriers. Suitable methods of administering such modulators are available and well known to those of skill in the art.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985))

Kits

MSC proteins and their homologs are useful tools for identifying mechanosensory cells, for forensics and paternity determinations, for examining mechanosensory transduction, and for diagnosing mechanosensory defects in animals. MSC specific reagents that specifically hybridize to MSC protein-encoding nucleic acid, such as MSC specific probes and primers, and MSC specific reagents that specifically bind to the MSC protein, e.g., MSC specific antibodies are used to examine mechanosensory cell expression and mechanosensory transduction regulation.

Nucleic acid assays for the presence of MSC encoding DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such a way as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, MSC protein can be detected with the various immunoassay techniques described above. The test sample is typically compared to both a positive control (e.g., a sample expressing recombinant MSC protein) and a negative control.

The present invention also provides for kits for screening for modulators of MSC proteins. Such kits can be prepared from readily available materials and reagents. For example, such kits can comprise any one or more of the following materials: MSC protein, reaction tubes, and instructions for testing MSC activity. Preferably, the kit contains biologically active MSC protein. A wide variety of kits and components can be prepared according to the present invention, depending upon the intended user of the kit and the particular needs of the user.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example I

Chromosome Mapping and Positional Cloning of MSC Genomic Region

To identify mutations with potential roles in mechanosensory transduction, a genetic screen was carried out to identify mutations in *Drosophila melanogaster* that result in uncoordination phenotypes. This screen yielded mutations in numerous genes. Further characterization of these mutations using electrophysiological methods determined that several of the genes also reduced or eliminated bristle mechanoreceptor potentials (Kernan et al., *Neuron* 12:1195-1206 (1994)). One of these mutations, responsible for the nompC (for no-mechanoreceptor potential), present on the second chromosome, abolished nearly all of the mechanoelectrical transduction in mutant cells. Flies with this mutation are uncoordinated to the point of lethality. Based on these phenotypes, the gene underlying the nompC mutant was identified as potentially encoding a protein playing a central role in mechanosensory transduction, such as a mechanosensory transduction channel.

To determine the position of the nompC gene on the second chromosome, nompC mutations were genetically combined with various second chromosomal deletions, and the resulting transheterozygous flies were screened for lethality. In this way, the chromosomal position of the nompC mutation was mapped to a small interval on the left arm of the second chromosome, corresponding to map positions 25D6-7.

To physically isolate DNA in the 25D6-7 region, the proximal-most clone from a chromosomal walk in the nearby 25D1-4 region (George & Terracol, *Genetics* 146:1345-1363 (1997)) was used to probe a *Drosophila* cosmid library (Tamkun et al., 1992). Overlapping clones were used to "walk" to the area that contained the nompC (MSC) protein encoding gene, by mapping the cosmid clones to genetic breakpoints. At the same time, the cosmids were tested for the ability to rescue the nompC mutant phenotype. One cosmid was found to rescue the lethality, uncoordinated behavior, and physiological defect of the nompC mutation. This cosmid was thus determined to likely contain the MSC protein-encoding gene.

Example II

Sequencing of the Rescuing Cosmid and MSC Gene

To determine the sequence of the cosmid containing the MSC protein encoding gene, the genomic DNA insert from the cosmid was isolated, sonicated, polished, size-selected, and the resulting 0.7-2 kb fragments subcloned into plasmid vectors. Plasmids were purified and analyzed for the presence and size of inserts, and 123 clones with inserts of greater than 0.7 kb were sequenced. The sequences determined from these inserts were used to assemble large contiguous fragments, which were extended by designing ad hoc primers from the ends of the fragments and using the primers to read additional sequence from the cosmid DNA. In this way, the entire 33.6 kb cosmid insert was sequenced.

The MSC protein-encoding gene was identified and characterized within this 33.6 kb cosmid sequence using exon analysis, BLAST searches, and secondary-structure prediction programs. These analyses established that the MSC gene is a large gene comprised of 19 exons, encoding a protein containing at least 21 ankyrin repeats and a set of as many as 11 transmembrane domains (6 of which show significant robustness), that is weakly related to the TRP family of epithelial cation channels (see, for example, Montell, *Curr Opin Neurobiol* 8:389-97 (1988)).

Example III

Sequencing of nompC Mutants

To assess the molecular defects of the nompC mutants, we used PCR to amplify the genomic DNA encompassing the nompC locus from flies with one of four mutant nompC alleles. In this way, all four alleles of the nompC gene were amplified in approximately 2 kb fragments that covered the gene interval. These fragments were then sequenced. All four of the nompC alleles showed mutations in the coding region when compared to the sequence of the cosmid and to the parental, wild type DNA.

In three of these alleles, the nompC (MSC) polypeptide encoded by the mutant gene was prematurely truncated in the ankyrin repeats by the introduction of stop codons. The fourth allele had a missense mutation between transmembrane segments four and five, resulting in a C to Y substitution.

Example IV

Identifying MSC-Related Genes in Other Organisms

To identify potential MSC-related genes in other organisms, we performed sequence comparisons between *Drosophila* MSC sequences and nucleotide and/or amino acid sequences present in various public databases. In this way, a previously unknown *C. elegans* genomic sequence was identified as an MSC homolog. This genomic fragment was found in the "unfinished/orphan" domain of the *C. elegans* genome project database. Using a variety of sequence analysis programs, putative coding exons, intron sequences, candidate transmembrane domains, and homology regions with *Drosophila* MSC were identified. FIG. 1 shows an alignment between the *Drosophila melanogaster* and *C. elegans* MSC homologs.

Three signature sequences for MSC, based on alignment analysis between the *Drosophila* and *C. elegans* sequences, were identified and are shown as SEQ ID NOs:7, 8, and 9.

What is claimed is:

1. An in vitro method for identifying a compound that modulates mechanosensory receptor activity in eukaryotic cells, the method comprising the steps of:
 (i) contacting the compound with a mechanosensory receptor protein, the protein having cation channel activity and comprising a sequence with 90% or greater identity to the sequence of SEQ ID NO:4; and
 (ii) determining the functional effect of the compound on the mechanosensory receptor protein, thereby identifying a compound that modulates said mechanosensory receptor activity.

2. The method of claim 1, wherein the mechano sensory receptor protein is expressed in a eukaryotic cell or cell membrane.

3. The method of claim 2, wherein the functional effect is determined by detecting a change in the membrane potential of the cell or cell membrane.

4. The method of claim 2, wherein the functional effect is determined by detecting a change in an intracellular ion concentration.

5. The method of claim 4, wherein the ion is selected from the group consisting of $K^+$ and $Ca^{2+}$.

6. The method of claim 1, wherein the protein comprises the amino acid sequence of SEQ ID NO:4.

7. The method of claim 1, wherein the protein is recombinant.

* * * * *

SEQUENCE LISTING

<160> NUMBER OF SEQ ID NOS: 17

<210> SEQ ID NO 1
<211> LENGTH: 24358
<212> TYPE: DNA

<213> ORGANISM: Drosophila melanogaster
<220> FEATURE:
<223> OTHER INFORMATION: genomic nompC (no-mechanoreceptor potential C) nucleotide sequence

<400> SEQUENCE: 1

```
gtgaccatgt tgcggggac  atgtttagta attgcaaaat cgatcaggtc tgggatttt      60
cttgggtctg ctggccagta tgtaggctta cccggggata attcgctctc ttaatgtgat    120
aatattaatc tcagaataat gaaaatgtca ttggtgtggg aaaatgtggg aaattgtcaa    180
ggaacgtaga gagtaacatg gtaattctat attttatttt tattttctg atggtaaaaa     240
agttctagct ttatagtaat aatatcatta ccttgagtta gtaagattta aaaaataaaa    300
taagctgcat tttaaaagcc acctttactg gttagacgac agcaacgata agataagttt    360
acattttgc tacttgcatc acttgttgcg gcatcactga taagcaaaca gacataattc     420
gcgtggctgg aggttttcct gattcctatc gctatatttc tgctcttatc atgcccccaa    480
aaaagttctg cccatactca agaattgct ttttatttag ttgaccttgt tgtcaaatca     540
gcaaggcata tttatatctg caattggaac tacaattgat gcataagaaa tgaggtgttt    600
gtgaatatct ttgaaactga acgaaagtt agtaacttag tttagtaact agtttgttta     660
gatataagtg agttataagt tgaattaaaa gaaggatcac ttcttctagt attgataaaa    720
ccatttatta tacagagagt tatagaagtg gctccatgta acctagacta gccaaaaaac    780
tattaggcat tcattttcct ggccacttgg gattttcgcg accagtcagc aaggatgaca    840
tactcccaat tgcgtctgtt gcccatttgg gtttcccacc ggcacttaac gacgttggaa    900
atcccaacga aacttaagag tagcgtccag attttggcgc caaaaaggc ggtattattc     960
ggattcaaca attgtaaaca aacgcttgcg cggatgccac ttggctctta cctctgattt   1020
ttcgcaggag cgtcttgggt ccttcgagtt tggagcttcg tcgtgttgcc agagctacca   1080
aaccgagtgg agggccgagt ttttccgctc gagcgccttg gaatagtcg actctgtgaa    1140
aatgggactg gcaaatcaga aactcgcaga cgctcgtggc aaacggttga ttttttctc    1200
gtcgctccga aaaaaggcaa aatagtaggc aacctgaaat ccagagttgt agttggggac   1260
tcttttggcc aaaatacaag gaggagaaaa atagaaaata ataaggggg  caccgccgtt   1320
aacgcacacg caaccgaagc cataaagggg ctaaacatat aaatttgtgt agtaaaagtg   1380
aagaaagcga aagaatcaaa gtggaataat agcgagtgtt tttcggtttg ctagtgtgtt   1440
tctgagtcgg agtttgtgtg tgtgtgttg tgtgattcct agtgtgtctg ttgctgttgc     1500
caatgaaaat gcaaattgtt ggtaacaaat attggtaaaa tgcggaggcc gtaggaattt   1560
gtgcaatgcg agtgcgaagt gaaggagccc gaaactatgc agctaaaaac ccgccatcct   1620
accccgcatc gaatcaataa taatacaata acccaaacgt attacacgga taatggcagc   1680
ataaaccagt taacatccga cagtgttttcc gcctaaccat cgagcaccta gctcatcccc   1740
cctgccacca acccttcgaa aaatcccat gatcagcgcc ggattgtgga gcagtaacta   1800
gcgaggcata ccaggatgtc gcagccgcgc ggagggcgtg gcggtgggcg tggcggcgga   1860
gtgggtcgca aaaccccctc ctcgctgacc ggcccaccgg atgagtcggc tacgcccagc   1920
gaacgggcta cgcccgccag caaagcagac tccgatccca aggacgatag ctcgagcaat   1980
ggcgacaaga aggatatgga tctttttcca gccccaaagc cgccgagtgc cggcgcctcc   2040
attcgggaca cggcgaacaa ggtgctcgga ttgccatga aaagcgagtg gacgcccatc    2100
gaggcggagc tcaagaagct ggaaaagtat gtggccaatg tgggcgagga tggcaatcac   2160
```

```
ataccgctgg ccggcgttca cgacatggtg agtactgtac agtgaagtgc cgcgaggcgg   2220
gctttccggc tcatttgcct cgttttgtaa aatcaattgc gagccaaagc gggaatagga   2280
agcgaaataa atacaggaac aggtccaaca ctcagcgaaa aatatggtaa attaaatgta   2340
tacctagaga aggattatca atagttttaa taaggttatt gaaatcttta aaactataat   2400
ttctatggat cttttagttg tatttatttg aaaaatttcc ttaagttttt gtgtaatatt   2460
tccctgagtg tatgcgatgt agaaacgtcg cccttatcaa cgtcggcggc attttcccat   2520
ttctggttgt ttaccagcca aaataacgac acaggaactg gaggccagaa aacagagcac   2580
accatggttt ggccaaaaaa cagaggctag caaggaaaag cgcccaaaaa aaaaaaaac   2640
agagaacagc gaatgttatt tgatagctcg gcccaaatgt tttggctgcc aaggcgatgg   2700
ctttggtggc attcggtttt gtagctccaa gttcctgaag cgtcctgcca caagttgcgc   2760
cgtatacgct ttggggttag ccccccgtcc gaccgataaa ctcataaaac atcgaagaat   2820
tgaagcgctt cgatttcaat ttaccataaa cgctatgaaa cggagaagtc gttgacataa   2880
aattaacgtt gcaccgctaa tgaaatgcgg ggaggtgtgc ggcgaagggt tgaaacttc    2940
ctggcagggt ttttcttta cttttttcct ttcctttttt tttttgtgtg gtactatata   3000
tcccaactag atgtgcaggt tgtctgctag actagactta cgacgagacg gtatttgcat   3060
aaatatagct tggagttgag ctattttgc cttgattatt tccgctttcc cagaacgggg    3120
gtctttattc ggttcttgac ttgatgggct tgctcttgat ttcgttttaa ttacgagcca   3180
acgagcttat aatatcacat ccagcttatt agccgaagga ttctaatgca ataaagatga   3240
atttaaatgg ccaagttgct tttcaatgag gtcagcgggt tggaaggaga gtaccatgta   3300
ttggtactat gttattgtgt ttaaaatgtg catatattaa tattgtatta ttcttacctt   3360
aagcttaagt aatccccata catttccatt gcagaatacc ggcatgacgc cgctgatgta   3420
cgcaacgaag gacaataaga cggccataat ggatcgcatg attgagctgg cgccgatgt    3480
gggagcccgc aataatgtga gtcttgagcg ggaatagggc aggaataatt taaagcacct   3540
tagccaactc cccacggtgt tggtgccaaa tatagaagcg gcccagctgt ttaagccaac   3600
ggcggcagca aaagccgcta aaaatgtgtc aaatcaataa aaaccgcata attaaatctt   3660
gagcggggc gttggtgggt aaactcgtgc acccacttct acgcacgatt ctcacacgcc    3720
gcccaccacg gtcaatactt caattcggca ataccctccct gccgcaatgg gtcaacttgg  3780
caggacttgg ccaatgggta gttcgcttca tttgactcca gttgagtcaa gttttccagc   3840
acgaatggga atttcctcaa gaaaagaaa tactaacaca ttgcttttat tttcatttta    3900
taactgctaa caaaaaatta taaactctta tttatagaaa actaaattat tattgggcac   3960
ccctcgtttt taagtggctt aaagttcgaa cttaactttg gttttaaag aaacagcaag    4020
tattactcat aataatgtaa ctcaacaaaa gagttttccc aaagagtaga gatgtaaggt   4080
catcgctgat gactatcctg atttccccag taatttacca tcgtgattat ggccaattct   4140
tttttttttt tgatgtcagc aagtgaagtg agccaggttg gcatcgccca ttaggccaag   4200
ttgctaacaa ttggtcgaat tcgccgacca gcttgctttg catgccgcaa ttacttagca   4260
catttcatt gaagtcgctt tcttggctgc ccattcacat gtccttacgt atacgcaacg    4320
tactttattt cggtgctagc ggcgataaaa atccttgacc taattacaaa ataattgttg   4380
ccaaaccagt gcagacatgg cgaattgaat taccaaaaca aacacagaaa gttcaatttt   4440
cccttcctcc ttgaaaatgt ttctcctaaa agattaaaga gtgtgtaggg aaaatgttaa   4500
aggtaaattt gcacatgaaa gtcataaaaac attaactagc cgggagttac aagctaagca   4560
```

```
tgaaaataaa acactcgata agactttata tgagtataag aatttatttt cgttttaaca    4620
ggacattcat tacacaaatt ttgccaatga tacttggtgt tttaaaatat tgagaaaatg    4680
ttgtccaaac tgcaactaaa aaccacatat atattaatta attatattta atataaactt    4740 tcccttttg caacacaatt aattatgata attattcatt ttaaaactgt tccatttgga     4800
tgattgttcc ctcttgttgt tcagctaatt aaatattatg atatcatttt cgtgagttta    4860
tacaaagcgc acctttttga aaaccattac ctcatctgta taattactct tttgtttta    4920 taaaacaaat gtcacttcgt gaccaaatcg gataatttcc cttacactga ccaaatgaat    4980
taaaaactga gaaatgttta ttgcatttac aattcgcaac ttatctaact gtcaggtctg    5040
gtccaaagta tacccaaac aacacgacag gaccaggacc tttatggcca ttataaagga     5100
tactcgtatg atgtaacgcc gtggtaatta acatttttaa cttttcaact gcaaggtggc    5160
agactgcttt tttttcggca ctcgacttgg aggcgtgctc gcaacacctc tttgcaacgt    5220
aaaagccaat taatcaagca catgactccg atgtacgccc agttggccaa aaactccatt    5280 tgaccttcg agtgtggccc aaaccggaga cctcgacgtc ggccccgact ccgctacat     5340 ttttatggcc agcggcgtca ttaatatgca attttaatta aattcaagtg gaattcttca    5400
cgcagtgacc cctgcatatg tgtgtggcga tgacagcgtg aactaaaatg aggaataaaa    5460
acgccaattc atttgtcaag ttgcctcagt gcgtgagtga agtaatctgc cccatccacg    5520 caaaaaaaa gcaaattaat tcacttcatt agaaagtggt gcacatgcaa gaaggtggag     5580
ggattaagcc aaatgagcac cgtaatgagg acttgcaatt attccaaaga aggtgtgtga    5640
catcgccaga aaatgacttc atggcttcca cgcgactatc cccgagtatc tctgggccgt    5700
aaaaacaaaa cacccacgaa actgggtcga cttcgtacac ccttatccac ccaaccttat    5760
cccttttcca tttggcaggg caaaaatgtg ctggaaaatt tgcgcttccg ctttggtttt    5820
gtttccggtt tttcctttcg accagccaag caaacgcaaa cacaagcgca caaacacaca    5880
agactcgaaa acgaactcga acctggctca aaagtatgca aaacagcgcg tgaaatatta    5940
tctgtctacc ttgacgcca atgcaacccc aaaccagcag cgattccgcc caccgcgcca     6000
agtggctgaa agtttacttt gcttttctt tagggccaac acgtcttgga tgggctttct     6060
ggacatgtgt caaagccgtc gactccgagc gccaacttgc gttgtatgca aattagcagc    6120
agctgcggcc agaaatagtc gcaaataaac cgcagggaac tcgaatttca cacggcacga    6180
agcccacaca cactgactta agtgggaaag tttgaaatac ccatttggat tctaggaatt    6240
gtaaaaaatc atgtgcaaga acacatagaa tgtataaata tagaattatt ttaaatggca    6300
taacttctgg tattctccta atttttaac atataatcta aactaagtat tattttcctt     6360
tcactatttt tattaactag aaattcgtat ccttttatgt tgaattttgt agactctgtc    6420
tgcacttacc aacctgatga cagggccaaa agcaccata catatatgct aaaccagttc      6480
acttccgttt tcgggctaa gaactgtggg gaggcttagt tataaattag agccatggtc      6540
cgaggtccga gcatacgggg cgtatgtgta acacgttgcg ttatggctta ttatataagg    6600
caataaatat ggccaaatgc ccccgattca tatgtgactc acttggctat tagctggcgt    6660
taaactaagc actccatgtc agacgttatc ttaaagcact tttcgttacg tttcggtgat    6720
ttgctcaggg tcatattttc ctagccgcat tgttttatat ttcttttcgg gttttcctgg   6780
tcgccattga tgcagttttt gcatgtgagt ttgcggctgg gctgtggcca ttaagaaaac    6840
cccgtccgta agtgaaagtc cgcatgcaag attgtggctt aagtaatcaa ccactccctt    6900
```

```
ttgccccgtt agccgcatgc aaaaccgact gactttgacc cattgaactg acccagctct  6960
tttggtgtgg gggcgtcagt ttcctgccaa tgaattgcaa ttgatttcct ccgttcttct  7020
cttctcttct cttttcagga t aattataatg tgctacatat tgccgcaatg tattcgcgtg  7080
aggatgtcgt caaattgttg ctaacaaaac gcggcgtgga tcccttctcc accggtggcg  7140
tgagtattcc aatagcttta tatactacat atatacgtat gcgccccaag aaagtgttac  7200
cccaatagtt gaggtagcga cacgtcaggc gacacactca atactcgagt tcctactttc  7260
gagtcaatga aatagctgca taccttgggg ctgctgtcag cccgattcgc aggcaatttg  7320
cggctattag acgcatactt cacctggctt cgaaagagaa gaaaaaaaaa aaacctatcc  7380
aaaggtcaga gccatgcgaa gatgcaactt tgaggctcgc atgttgcatg ttactttggc  7440
gggaccagca attaactggc gacaaggtta agatggtaat gtctagggcc cgcttaagaa  7500
cactttaaga cctgaaaaca aatttaaagt aaccctaggt ttcacgaaaa actttactca  7560
tcagattaaa cagaaattta agcttagata ccgtcattaa aattaaaatt taacattttg  7620
catgatttcc aagtctgact tctgtttaaa tactacaatg tataaatatt aaagtctgag  7680
caagattagt gacaccatct ttatattgtc taaaatcata aagcgttaac catttaatac  7740
aatgcatttt ctcataggta acattttaa caaaatatat gatgatcaca tcgtcaagca  7800
ttttggcaat tatttctcca agtttatttc tcgtgtcggc attaatttgc ttttctttat  7860
tttttctcg gccgcattgg gttttcgaga cttggttatt taggggcgt gcgccttgcc  7920
caaattactg atggttatca gaagagagct ctaagcacgt gtgggagcga gagaagtgga  7980
gctgcggaag cgagacagac agatgcaaac ttttgtttta gcaacagcca agtttgaagt  8040
gttccgttag cgtgtgtgcg tggcaaaaag gactcccaca tccacaaccg acacctgccc  8100
cccatgttgc ctacacctgc tgctcgacca cccctccccc accatcacct atatacacct  8160
ctctcgctca ctcccgcagc ggttgtcggt gggagttctt tattatgctt ttttcgggct  8220
gtcaatctgt gatatgagcg ggagaggcca aaaagaaaa atgacacgaa atgtgcttat  8280
aaacgcaaaa acgagccact tgcctattca gtagcaaatg gaattttgaa gcgaataggg  8340
aaacagtttg ccagtttttt aggtgccaac attaaccaca cagtagtgca catagctgca  8400
tattaatttt ggctagaaaa aaagtgtaac cccagcaata agtgcgtttg cagtgtgtgc  8460
atagtttaat cgaagactta attggatttt tttcccttt cagtcgcgtt cgcaaactgc  8520
ggtgcatttg gtgtccagtc gacaaaccgg aactgcaact aatatcctgc gcgctctgct  8580
cgcggcagct ggcaaggata ttcgcttgaa agcggacggc gtaagtgtta ccatgtgtgc  8640
ttgtgattga gtgtgccagt gtggctgtgt gtgtgcgacg gagagccaca agtgttggcc  8700
gcccaattga tgccgcttta tctccactag tttatgatag ctaagccacc caaatgcaag  8760
ccgatgtgaa gtcaagtact ctcgacagcg gtgccaggcg gtgccgacgt aaacaaagac  8820
ttaataaaaa tcaccaaaaa atatatacat tacaataatg gcaccaacaa atcgagagg  8880
agttagtaac ataaagcaaa caaaattgtg tggaaaaatc gatatgcaaa actgctcgcg  8940
gtaaatgcat ttcgactggc tgtaaatcag aaaaggccca aaaagttaa tgcggctatt  9000
acacagcgag gaattgaata ggtaatttt gagtcaattt tagcttataa tttgtggtac  9060
ttttatgaat ttttttaaaa ttttattttc aaattattag agagctaata tatttgaatt  9120
atgcttatat aacttaaaat actcaaaatt tatagacagc aataaagtat gggatctgca  9180
acacatcttt ttctacactg tatcaataag tagctctcac cacagtgggt aggctccagc  9240
gagctttgaa ttaccatcga agcagttgtc tccgcctgat gaacttgctg gggctaaccg  9300
```

```
agctccagat cccttttcg agctcccccc ttggaaatct gaacagaaat gcggaactat      9360
ttgtcgcatc acgtgccccg ggtgaaaatg cacaggcgat atttccatta cgcacgcgaa      9420
gaaagcgcat aaatttccaa cgaattgcta tcaagcgatt gtaaggattt ggggtatatg      9480
ggggctgatt gagggaatcc cgggtgccac cgattgattg tctagacaaa atgggtaacc      9540
cacctcgatt tgtgcctcga gggctgcggc aaatggcaaa cagcaacttg atttaaatca      9600
attagagaga ggtggaatgg cactgtcagg cgaaattagt cggatgaagt atttagcttt      9660
cgatggcatt cagttcgatt cgtttcgatt cgcttttctt ttttttttct acacgcattt      9720
ccggtgtgca tatacatgca aatatatata ttgtatgtgt gtggatagta ctgtagtttt      9780
cccccgcgag ggcgctcaac tcgttgccaa caacaaacaa atataacaaa gcgaggaaaa      9840
ctctaccgaa aaagggggt caagtcgctg tacaacttga tttactcgcc tttcctggca      9900
gatagggata atggctcccc gtcacgcccc cctcttacga ctcgccccca aaaggtagtt      9960
ggttgcaagt tggagcgcca aagttgcgaa cttggctaaa aatagcgaaa catgttgccg     10020
ttaacacttg aggctcgaat tggctaattg gatatttatg attatatgtt cgcgagtgtg     10080
aatggatgtg tgttcgctgt ccttatctta attatatttt atactatata taacctatct     10140
ctaacctagc gtggcaaaat accattgctc ctggccgtgg agtcgggcaa ccagtccatg     10200
tgcagggagc tcctggctgc acaaacagca gagcagctca aggtaagtaa tctgtgaact     10260
agcagataag tttacccact tattttaaaa cctaaaagtc tagttgcagc ttatattgat     10320
ttaaatagaa acactgaata catcatctag ttaataacca aaaatgtcaa cagtatgagc     10380
cattaaaagc ataaaatgct aatttcttat accatctacg catctaactg atttcctaac     10440
taggaccaag aaattgttga ttttataatc gccacgatag tgtcaatcaa actgtccatc     10500
tgagctgtcg gaaaatgtcc acaaggttct taaagccttg aactgtccaa taaccaagcg     10560
tgtaaataaa tcaaaaatgc aaatttaccc tgctcacctg tgcgtacagg tgcattgcaa     10620
gtgcaacagt gcgcgacatt ggcaaagttt gtgcaatttt caatcagaag ttgaagtgca     10680
acacaccaag agcagtgcgt gttgattaaa ttaaccaaag ggctacggct cgcttcaggc     10740
caagggttca agcccaagtt aaagttaaag ttgcgcctga ctttggccgc tggctgagca     10800
cgcaatcagc cggcaaaaca gccgtaaact gggtcaaaac tgaggcgaaa acgcagctaa     10860
gatgggaagg gaatctgatt tgcatagccc aaaataaaat gtcgaaagtg aaatgcagca     10920
acactaagga aaaatttaag taaattattt aaaaatattt aaacaatgaa gctatgaagc     10980
tctagcaaag ataccaattt agttagggaa tatcattata atttgtcaca tagttaatta     11040
atttcaagca taggagcaat tatgactttg caattatata aaaacatttt tgtgaagtgc     11100 acccttcat gttaaatttt ggatttattt tttcgcaggc aacgacggcc aatggagaca     11160
cggccttgca tttggccgcc agacggcggg acgtggacat ggtccgcatc ctggttgatt     11220
acggaacgaa tgtggacacg cagaatgggg agggccagac gccacttcat atcgcggccg     11280
ccgaaggcga tgaggctcta ctcaagtact tctatggcgt gcgcgcctca gcgtccattg     11340
cggacaatca aggtgagtct gtgggaatgt ggagcaagga aaagcatgtt gcaaatcgtg     11400
tttgaccttg ataacaca ataaaaatca tgaaattttc acttctcaat agaagctagt     11460
gattataaag tggaggtata aagtatatgt ttgtggcgcc cccggttgga ccgagctcca     11520
gacatacgaa tgtccgtctt gatgattaaa atttatatat atatatatgt aatacccctat     11580 agatcgcact ccgatgcact tggccgccga gaatgggcac gcgcacgtca tcgagatact     11640
```

```
ggccgacaag ttcaaggcga gcatcttcga gcgcaccaag gatggcagca cgctgatgca   11700
cattgcgtca ctcaacggtc atgctgagtg cgccacgatg ctcttcaaga agggcgtcta   11760
cctccatatg cccaacaagg atggagcccg gagtattcac accgccgccg cctatggtca   11820
cacgggaatc atcaacaccc tgctacagaa gggcgagaaa gtggatgtga ccaccaatgt   11880
aggtgggata atgtattaag ggataatcgt attaattcca cactctttgc aggataacta   11940
tacagcactg cacatagccg tggaatcggc taagcccgcc gttgtggaaa ccctgctggg   12000
atttggagca gatgtccatg tccgtggcgg aaaactacgt gagacccgc tgcacattgc    12060
ggcacgagtg aaggatggag ataggtgtgc cctcatgttg ctgaagtcgg agccagtcc    12120
aaatttgacc acggatgact gtctgacccc cgtgcatgtg gcggctcgtc atggcaatct   12180
ggccacgttg atgcaactcc tcgaggacga aggagatccg ctgtacaaat cgaatgtgag   12240
tagattatta aatagaatg ataaacgctt gaattaaaac ttccatttta tagactggag    12300
agacaccgct gcacatggcc tgtcgtgctt gccacccgga tattgtgcgt catctcatcg   12360
agacggtgaa ggagaaacac ggtccggata aggccaccac ctatataaac tcggtaaacg   12420
aggacggcgc cacggcgttg cattacacct gccaaatcac caaggaggag gttaagattc   12480
ccgaatccga caagcagatc gttcggatgc tcctcgaaaa tggtgcggat gtcacgttgc   12540
aaacgaaaac tgccttggag accgcttttcc actactgcgc cgtggccggc aacaatgatg   12600
tgctgatgga gatgatctca catatgaatc ccacagacat ccaaaaggcc atgaaccggc   12660
aatcatcggt gggctggact ccactgctga ttgcttgcca tcgagggcac atggagctgg   12720
tcaataatct actggcgaat cacgctcgag tggatgtctt cgatacggaa ggacgatctg   12780
ccttgcattt ggctgctgag cgaggatacc tgcatgtgtg tgatgccctg ctgaccaata   12840
aggcttttat taactccaag tcccgcgtgg gacgcactgc actacatctg gcagccatga   12900
atggatttac gcatctggtg aaattcctga tcaaggatca caatgcagtt atcgatattc   12960
taacgttgag aaagcaaacg ccgctccatt tggcggcagc cagcgggcag atggaagtct   13020
gtcagctgct cctcgagctg ggcgccaata tcgatgcgac ggacgatctg gccagaagc    13080
caatccacgt cgccgcccag aacaactact ctgaagtggc caaactcttc ctgcagcagc   13140
atccatccct ggtgaatgcc accagcaagg atggaaacac atgtgcccac attgccgcca   13200
tgcagggatc cgtcaaggtg atcgaggagc tgatgaagtt cgatcgatcg ggtgtgattt   13260
cggcgcggaa taaacttacg gatgccacgc cccttcagct ggccgccgag ggcggacatg   13320
cggatgtggt gaaggctctt gtgagagctg gtgcctcctg caccgaagag aacaaggcgg   13380
gattcaccgc cgttcatctg gcggcacaga atggacatgg tcaggtcttg gatgtgctga   13440
aaagcacaaa ctcactaagg atcaatagca aaaagttggg tctgacgccg cttcatgtgg   13500
ctgcctatta cggacaggcg gataccgtgc gggaattgct gaccagtgtt cccgccaccg   13560
tcaagtcgga aactccaacg ggacaaagtt tatttgggga tctgggcacg gagtccggaa   13620
tgacaccact acacttggcg gccttttccg gcaacgagaa cgtggtgcga ctgctcctca   13680
actctgcggg tgttcaagtg gatgcggcga ccatcgagaa cgtaagatta cctgcatatc   13740
tcttctgttc agaaaccatt aacacaacaa ttgattctac agggctataa tccactccat   13800
ttggcttgct tcggtggtca catgtcagtg gtcggtttgc tcctaagtcg gtcggcgaaa   13860
ctcctccaat cgcaggatcg taacggcagg acgggcctgc atatcgccgc catgcatggc   13920
cacatccaga tggtggagat tctgctcggc cagggcgcgg agatcaacgc aaccgatcgg   13980
aacggttgga cgccactgca ttgtgctgcc aaagctggcc acttggaggt ggtgaagttg   14040
```

```
ctgtgcgagg cgggtgcctc gccaaaatcg gagaccaact acggttgcgc cgccatttgg    14100
ttcgccgcct ccgagggaca caacgaggtc ctgcggtatc tgatgaacaa ggagcacgac    14160
acctacggcc tgatggagga caagcgattc gtgtacaacc tgatggtggt gtccaagaac    14220
cacaacaaca agcccattca ggagtttgtc ctggtatcac cagcacccgt ggatacagcc    14280
gccaaactgt ccaacatcta catagtactc tcgacaaagg tgatttagct aaaggatctc    14340
tatgcactta actaaactaa ctaactaaaa cattttgatc tctttaggaa aaagagcgcg    14400
ccaaggatct ggtagcagct ggcaaacagt gcgaggcaat ggccacggag ctcttggccc    14460
tggcagctgg gtcagattcc gccggaaaga tccttcaagc caccgataag cgaaacgtgg    14520
agtttctcga cgttctcatt gaaaatgagc agaaggaagt gattgcccac acggtagttc    14580
agcgatactt gcaagtgtgt gatattattg actagcttag atcttaactt attgagattc    14640
tgatatgtat ccttcttcct acttttagga actctggcat ggctccctga cgtgggcatc    14700
ctggaaaatc cttctgctgc tcgtggcctt catagtctgc ccaccagtgt ggattggatt    14760
cacattcccg atgggtcaca agttcaacaa ggtgcccatc atcaagttca tgtcgtacct    14820
aacctctcac atttacctca tgatccacct gagcatcgtg ggcataacgc ccatttaccc    14880
agtgctccga ttgagtttgg tgccctactg gtacgaggtg ggtcttctca tctggctgag    14940
tggattgctc cttttcgagc tgacgaatcc gtcagataaa tcgggactgg gatcgataaa    15000
ggtgctcgtg ctgctgctcg gcatggccgg agtgggtgtc catgtctcag catttctatt    15060
cgtctccaag gagtactggc caactttggt gtattgtcga aatcagtgct tcgcgttggc    15120
cttcctgctg gcctgtgtgc agatcctcga cttttttgtcc ttccaccacc tattcggtcc    15180
ctgggccatc atcattgggg atctgctgaa ggatctggct cggttttttgg ccgtcctggc    15240 catctttgtg tttggctttt ccatgcacat tgtggccctg aatcagagct ttgccaattt    15300
ctcaccggag gatctgcgca gcttcgagaa gaagaaccga aatagaggct acttcagtga    15360
cggtaagtcg aaacgtttgc tttgctttct ccagtctact tttcgaattt ttgtttcgaa    15420 cttttttgttt tcatttggaa tgtttttgca aacttcctct tttgaacgtt caatgtgtct    15480
tgataagtat ctgtgtctgc cttgaatgaa aagcccctct aatcaatgtg cgctcgatgt    15540
ttcacataag taaaataaag caaaaaagaa ccaacttcaa ccacataata caacaattgc    15600
atgctcaaca agtacaaaca acccgaacct ccaaccttga tgtcgtaatc cccgtccacc    15660
cctccaccaa aagacctcca ctaataatgt tctccctctg atcttaaccc ccaactgaat    15720
atcttaactg aattatccga atggaacaga tgacatgccc acaccccgac ctccgccggt    15780
ggagaattat gtcgatagtc gcttcagcga attccgacga aagcacaagg acgaccgtaa    15840
gtctcctacc atccacaact accaaccctt actaccccg catttgcatg gccccccttt    15900 ccggggggctg ccccgccccc ttaacccaac aatgccggaa tccaaaccgt tgcgttgccg    15960
ccttcgatgt tgtgcgtaaa gtgttaatgt cgtttgtttt ctagttccct ggaggaacat    16020
ccacaagtcc gcactcgctg ctcgaaatcc cctcgccttg ctagtttcag ttactttcgt    16080
tttgaggcat gttcgcggga aaatcccttt tccgcatcct cgatgttgtg gatctgtgtt    16140
tatataggta tccatgcgcc aagctttatt acttagtttg gagtatcgtt ttataccttt    16200
gcttggatca attttaattt atatgtattt ctttatgtat ttttaagtga catataaata    16260
caaataaatt attaagaatc agaatttaaa accataattt attctcatta aattcaatca    16320
ttattatttc aaaaaatcct agatctgtgt ccgatattat tttctttact atatttgtta    16380
```

```
ttcttttttt aagttagatt ttttatcgat gtgtaaccag agcgatatcc attagaactc    16440
tgtacaaact aaaaattcca gtaatgcatg ttgatgtttt tatccagtca atccaaacca    16500
aaatcaaaca atcaatcagc aatatcgata taaccaatgc ccgcctgcct ggggctttca    16560
gcttgcgccg cttcccacc accaaattct gcacaatcga acaatcgag accgatcgaa      16620 tcgaatcgat aacgaaaaac gataacgcta ctgataccga ttaccgatgc tcgtattcgt    16680
gagtcattcg aaccgctcag ctgcgaactg cgagatgctg cttttgacgt gtttaaccac    16740
tcacccgcac tctccaaaat ccaaataaac ccacccataa atatactcgt ttatgtaaac    16800
ttcaaaataa ccaacaaata ccaagtatta aactcgcaca cacgcctgtg ccaagccgac    16860
aatatatata cgtatatata cgctagctgc agcaatcgca atgcaatagt tcagttatct    16920
gattgtgagt aacgttccgt tcggacccat gttaggaccc atgacgccct ttctggcttt    16980
cgagcgcctc ttcttcgcgg tcttcggaca gacgaccacc ctggacatca atcccatgcg    17040
acacttgcgt cccgagtgga ccgaggtgct cttcaaattt gtctttggca tctacttgtt    17100
ggtgtctgtg gttgtactca ttaacctgct aattgccatg atgtcggata cttatcagcg    17160
cattcaggtt tgtattgcca aggccactaa tcagtatttt ctctctgctt tccctcttcc    17220
cccgtttatt tgtttcaatt ttcatttacc ggaatgctat ttgtttgtgc tttgattgta    17280
acaaccccaa aactgaccgc tccaaattga aacacaattg ggcatgaacc gaaactgggg    17340
gttggtcgat cggacaaatc aacgaaacaa aaaaaaaaaa aaaaaccaca taatcgaatc    17400
aaccaaccca acctgggcgt ccgttatctt tttatttttc aaaataattt ccacgccggc    17460
caatatatgc gtgctgtccg ggggtgtcta tttgtatctg tatctgtatc tggaaatgta    17520
tctatgggtc tccgacacag tgcgcatgca tccgattaac tcgttcgagt tgttgttctt    17580
cgccgtgttc ggacaaacga cgaccgagca aacgcaagtt gacaaaatca aaaatgtagc    17640
cacgcccact caaccgtatt gggttgagta cctgttcaaa attgtctttg gcatttacat    17700
gttggtgtcg gtggttgtgc tcattaacct gctgattgct atgatgtcag acacctatca    17760
acgcattcag gtagtattgc taaatgcgct tttatctaac tcgactctat ttattaactc    17820
gtactttaac cataagtata taaatttcat attgcattgt gtattaatca ttctctattt    17880
cagcataaga agtaaattta catatgaaga tgatttatat ttcttagata tataatagcg    17940
gtagttagga agtgagctgt tttgggaaca tattgagaaa atagttaatt aatctggaga    18000
acttggcatg ctctgtaaat ccatcaactg cccagacttg catcttccag gttttttcag    18060
gaaaataatg ttagcaatct gagggataca attttgtgaa agtgtatctc aaagatggaa    18120
gcctgccgcc ttctagtgta gtacagtgca gagtagcttt agtggattag ccgccttgaa    18180
gtgtgccctg cttttgtgac cagtgttgag cgaggccaaa ccagaaagtg ttggttaacg    18240
catgcttaca aaaccttata tatagaaatc gttgctgcat gcttatatgt ctgtgtttgt    18300
cattgtctag gacttaagtc tgaagagata caccaatatg gtggtaggt tttgtatggt     18360 aattttgtga ttgccatcca aaacaggcct ctgaatttgt gtatttctat tattaacaac    18420
ctgatttttg cagctcttaa gttacgtatt aacaaagtaa aaacctgtaa atccgaggc     18480 ttctgttcac gaaactcatc ccgtttattc ctttgttctt gttctctcct atatcatgtc    18540
tcatccatcc aacatcgcgc acctcgctaa ccaataataa actgaacaaa aaaaaaaacc    18600
tatgaaatac taggcccaat ccgacatcga gtggaaattt ggcttgtcca agcttatacg    18660
caatatgcat cgcaccacaa cagcgccatc gccgcttaat ttagttacca cctggttat    18720 gtggatcgtc gagaaggtca aggtaaaatc tcaggtgacg aaggtcgcct tccagccgct    18780
```

```
gtcgctgtgt ctctctctct ctatccgtat cctgtatcct gtatcttata cctgtttcca    18840
tatctgttga ctatataaag tgcaactacc agaaccgatc ctgaacgggt gtagtttgct    18900
gaccttttcc ccaacccatt taaagcaatt tggcaacaac cgcaatgagt ttgaacacag    18960
tgaatgcttt aagtgtgttg cccacataag aaaatcacct tgtcaccttg cactttctct    19020
gtaacttcaa aataggagat cgaaatatag gtatgtaaat gtttcgatcc cctacactgt    19080
atggcacttt atgtccagca cttggcaccc gattgctttc gatgtaatga acatttgctg    19140
actgcgttta tgttgtgtct cttgtcttgt atgtgatcta tgtcccgtgt ctaatgcgcc    19200
ttgatctaac ccacaaaacc tgcaaacaaa tcctgcaaac cgcaattcaa aaaacacgcg    19260
cctcaggcac gcatgaagaa aaagaagcgt ccaagtctgg ttcagatgat gggaatacgt    19320
caggccagtc cgcgtaccaa agccggcgcc aagtggctgt cgaagatcaa gaaaggtgag    19380
acatgtatgt atcgctgctg ggctactccg accaggatcc gtccatatcc tggaaaacac    19440
aacccatcca tccgaggggt tttgtagcta acagcgtgtc agcccaagtg taactcctaa    19500
ctttccttca actcaactct tttctctgga acaattggct cgctctagct cgaaattatt    19560
tcctcaacct ttcgcctttc cagtgcacaa aggtagaaac gccatggatc tctataaatc    19620
cgacattata ttgaatttga ggtagaagtc gtgatctttg gcgtttgtac ctcagtgcat    19680
cttgctgtat agtggaatcc aaaagctaat gatattacct cgaattccca gactcagtgg    19740
ccctgtcgca ggtccatcta tcgcctctgg gatcacaggc gagcttctcg caggccaatc    19800
agaatcgcat cgagaacgtg gccgactggg aggcgattgc caaaaagtac cgggcactgg    19860
ttggcgacga ggagggtgga tcgctcaagg actcggatgc ggagagtgga tcgcaggagg    19920
gtagcggagg acaacagcca ccggcacagg tgggcagacg agccatcaag gccaccctgg    19980
cagacactac aaaatagaca cacagaaatg acacagaaaa aacagaaaaa cagcttcgga    20040
tgcttaatta actacgtttt gattgcaggt ctaagcttca tctatctctt caaactatcc    20100
ttcctgacta tctctatctc ttctcgacta tccaagcgtc tgtccttctg taattctaag    20160
atctaactct aagaaactct atccgtaagc tgcaccttgg gtatggtttt ctcagactct    20220
ggaacccact tcttttggtt caactggagt atgggaaaat cagactaaaa tccttaagtt    20280
aagccttcac tttctaaact aattttagct agaatattga aattgttttg agtaacccttt    20340
aaagcgaaag ctgattgttt atttttgatat gattttccgt tggagttttc tacgattagc    20400
gaaacaacaa aaaaaagttt tccatgttcg agatttttaa agtaagttaa ttcgtccttt    20460
ttggactcaa tttgccttac attttttgaa accaactcct agcattttgt attaagctaa    20520
tgattgcgac catatcgtta ataatgattg tcttagagat gttaagtaaa ttgaacttta    20580
gcttcaatcg gagctaaaag tcaagcggtt ttatataaat ctcgcataat ctcattgttt    20640
tccggtaatt gtcaagtaac aacgttcact ctacttacta agctttggtt catttttat    20700
aacaaatgag cgcataaaat tgttaactgt acttgattgt aaataaataa gtcttatttt    20760
aaaatattgt actattgctt cagcttgtaa tcattgcata cttttttggcg gcactggcat    20820
ataccgccat ctatcggagg aaacaaaatt ttaaaattat gtttagcatt attttttcta    20880
attaaactat ttttgggttc atgccttataa tacaattata attttataat tataagtctg    20940
tattttttgaa taaatggatt gttttttgtgt ttgttattta tatcgtacgt tactcgcgtg    21000
ctgccagatt atcaaaaata gctctcgctt atttcccatt cacttgagcg acatctgtga    21060
atgaaatata gaacatgcgg ataaggtatt ttttggtttt cattaaattc cgctaggtgg    21120
```

```
cgaatgcaaa tgtaaaatta atgtaaattg ataaatcatt gaaactaatg attaaaaaaa   21180
attgatttag aatttaataa tatatattgt attttgaata atatttccta aacctttcat   21240
ttaaataaaa atgattacga ttttatcata aatgttggtt tttattctaa cttagtaact   21300
gcaagctggt ttgattatgc caagataatt tcaaaatagg ctagaattct ctcctttaaa   21360
ccatgtaatc atggccataa agctaagaac gggcaataaa attcgcttaa tttgcctgct   21420
gaattgacag attaccaaga ggcactcagg cgtcattagc cgggccagca gaaaagcgac   21480
agaaaccgca tcggaaattg accaaggtgt tgaacttcgg aattgcattt taatttggct   21540
tcaagctgca gtttgctgtt gttttcgcct cgattgcagg tgtcacagtc ggtttaaatg   21600
tgttgaaaac ctcaagtggt caatgtttgc tgcttgctgc actcgcactc gtattattac   21660
acataattgc cccttgccgt tgacattgtt gctgtgtggc agttgcactt gcatttgcag   21720
ttgctgctgt gcttgatatt tgccaccgat aaaatgcata catacatgca aaaatatatg   21780
aaaacgaaaa gcaaacgagt ttctgtagcc gcagccaagg tttatggcca caagcgtgtc   21840
aatttaagct gcaattaggc agttaataaa tttaaccgat cttaccagtc agataccagg   21900
tccagatgcc agctgattaa tgccactttc ccagcgattc ggtagctgca acgtacaaaa   21960
ctccaaatgg attccaatcg gattcgatgc tggcgatgct gtggctgtcc gtcatccatc   22020
aaaggtttct tctacggacc aggaagcagt ttcgattcga ttcgatccgg gcttccatgg   22080
cttcagcctc cgcgactcgg catcgtgcaa catgtgtgtg gtgtgttggc acagcaggtg   22140
acatttccag gccagatcag gaaaatgtaa ataaatgatc ggacattgga cgacacccat   22200
gcccataacc ataccccatat gatcaacctg gctgaacacg catggagca agttgtacct   22260 ggttatacga ctatatgttg ctgttcatgt tgctgttgct ttgatataca aaacactttt   22320
tcatatcgaa atttgtgata ggccgtgatt aatggcgagc gacacaaaca cttaatttga   22380
cgccaggccc gtagctggcg ccttggggaa atggcagaga tccgaacgca aactcttttgg   22440 gtgcacagag agaaaagatg ctaattttcc attaaaagta tttagtatca gcttgaatga   22500
taggtaggtt actgttaaag cgtttctgtt gagctaatag gcattaataa atgccattga   22560
acaactaaca tttaagacta ttttataagt aatgagatca taaatagtaa aaatgtagtt   22620
acctcttttt ttcatcctgt agctttgaat ttgctgctgg tttgctggct gggagaaaca   22680
ataatctcgg gcaagattaa ttattgtaat cacatcaaca gcagagccat gcgaacggat   22740
tctcgtattc gtattcgttt tcgttttcgg aatgggagtc acagaaaaac caacacgaaa   22800
atgatcaatg atcatcgctg ggttctctgt tgattttat agcgaacgcc cgatcgccgg   22860
cctgggttac acatttcatt ggctaatcaa gatgctaatt tgaagaagat taattcgtgt   22920
gcgagtttct gactgcctgc caggcaagcc cgaagattcg aagattataa tctgctaagc   22980
aagaggaaac tgaaggctta ttattaatac aggccaacac agcccccaga aatgtgtctt   23040
gtatttaatt aaatacgcgc acactgggaa aagcaattcc aatgaattct taatctatttt   23100 tctaattttta taggacatta aaaccatatc ttaaaataaa aactcttgta tcgaaatcat   23160
taaaatgtta tgcttacttg caaagactta tcaccatttt tttcgcgtgt atctgccatt   23220
tagccacatc ccagaaatgt ggagagtttc gggtgagtgt tggcttggca gtgcagtgac   23280
acgcagatta attgaaattt tatgagtagc gcagacgtaa acaatcagcg agaccacctt   23340
ttgccagccc cttaggtcat aggagctcgc caagatcccc ctgctcggat ggcgtatcca   23400
tgtccagatt ccaagctcca gcttgactac actaactggc caagtcggca acggacagct   23460
gtggctcacc ccgtggccaa aagaaacttg caacattatg aaaaatggac cacagccatg   23520
```

-continued

```
cacagtggtt gacagcagac ccttgggatg tgtggaaatt atttggaagc aacagcaaat    23580
aattccagat aatgcaatta attcgatact tatatattat attctatatg tattttagta    23640
ttttaaagaa cttctgttga taccactgtg ccctgtgatc ctgctgacgc gatcgccacg    23700
ctaattgata gactgtgaaa ttatttaaca acggctggaa agtgagctcg gcgtggctgc    23760
ggctcgaaag gagcttccaa gcgtggccag atgggtcaga aggctttcga cccgccatc    23820 aagaccaggg tcggcacatc ttttggtgg ctctggtccc tggccgctgg ccaatcatcc    23880
atccagtgga ggatcgcgga cttacggcta agtgaaaagt gttaaaaagc acgactcacg    23940
gcgggcagtt gtgtcggatt tgaagacaaa tgagcagcgt cttttgacat ttgcgaaatt    24000
taaaatgtca gccgaaaact ggtgggtcgt ccacccttga cgaaggtttc ggatgggagg    24060
tcccggttcc atagcggatc gccacgcttt gccggataag tcgcggagaa tttaaattaa    24120
aactcaggtg aaaggttatt aattcgcaag tggaactggg gcgtagctcg gctcactgtt    24180
aatactcgaa atctccactc atttgggtta atgctgatgg cactttgaca gggatgatga    24240
tgatggggat atgacgaatg ccagcggcga tgatgccaaa taaatggaa gtgacagagt    24300 tcagtgcgtt ggttttaatt aataagcata tttccagaga gctttctttt cagcaaag    24358
```

<210> SEQ ID NO 2
<211> LENGTH: 1704
<212> TYPE: PRT
<213> ORGANISM: Drosophila melanogaster
<220> FEATURE:
<223> OTHER INFORMATION: amino acid sequence derived from nompC genomic
      sequence

<400> SEQUENCE: 2

Arg Thr Pro Met His Leu Ala Ala Glu Asn Gly His Ala His Val Ile
  1               5                  10                  15

Glu Ile Leu Ala Asp Lys Phe Lys Ala Ser Ile Phe Glu Arg Thr Lys
             20                  25                  30

Asp Gly Ser Thr Leu Met His Ile Ala Ser Leu Asn Gly His Ala Glu
         35                  40                  45

Cys Ala Thr Met Leu Phe Lys Lys Gly Val Tyr Leu His Met Pro Asn
     50                  55                  60

Lys Asp Gly Ala Arg Ser Ile His Thr Ala Ala Tyr Gly His Thr
 65                  70                  75                  80

Gly Ile Ile Asn Thr Leu Leu Gln Lys Gly Glu Lys Val Asp Val Thr
                 85                  90                  95

Thr Asn Asn Tyr Thr Ala Leu His Ile Ala Val Glu Ser Ala Lys Pro
            100                 105                 110

Ala Val Val Glu Thr Leu Leu Gly Phe Gly Ala Asp Val His Val Arg
        115                 120                 125

Gly Gly Lys Leu Arg Glu Thr Pro Leu His Ile Ala Ala Arg Val Lys
    130                 135                 140

Asp Gly Asp Arg Cys Ala Leu Met Leu Leu Lys Ser Gly Ala Ser Pro
145                 150                 155                 160

Asn Leu Thr Thr Asp Asp Cys Leu Thr Pro Val His Val Ala Ala Arg
                165                 170                 175

His Gly Asn Leu Ala Thr Leu Met Gln Leu Leu Glu Asp Glu Gly Asp
            180                 185                 190

Pro Leu Tyr Lys Ser Asn Thr Gly Glu Thr Pro Leu His Met Ala Cys
        195                 200                 205
```

-continued

```
Arg Ala Cys His Pro Asp Ile Val Arg His Leu Ile Glu Thr Val Lys
    210                 215                 220
Glu Lys His Gly Pro Asp Lys Ala Thr Thr Tyr Ile Asn Ser Val Asn
225                 230                 235                 240
Glu Asp Gly Ala Thr Ala Leu His Tyr Thr Cys Gln Ile Thr Lys Glu
                245                 250                 255
Glu Val Lys Ile Pro Glu Ser Asp Lys Gln Ile Val Arg Met Leu Leu
                260                 265                 270
Glu Asn Gly Ala Asp Val Thr Leu Gln Thr Lys Thr Ala Leu Glu Thr
            275                 280                 285
Ala Phe His Tyr Cys Ala Val Ala Gly Asn Asn Asp Val Leu Met Glu
        290                 295                 300
Met Ile Ser His Met Asn Pro Thr Asp Ile Gln Lys Ala Met Asn Arg
305                 310                 315                 320
Gln Ser Ser Val Gly Trp Thr Pro Leu Leu Ile Ala Cys His Arg Gly
                325                 330                 335
His Met Glu Leu Val Asn Asn Leu Leu Ala Asn His Ala Arg Val Asp
            340                 345                 350
Val Phe Asp Thr Glu Gly Arg Ser Ala Leu His Leu Ala Ala Glu Arg
        355                 360                 365
Gly Tyr Leu His Val Cys Asp Ala Leu Leu Thr Asn Lys Ala Phe Ile
    370                 375                 380
Asn Ser Lys Ser Arg Val Gly Arg Thr Ala Leu His Leu Ala Ala Met
385                 390                 395                 400
Asn Gly Phe Thr His Leu Val Lys Phe Leu Ile Lys Asp His Asn Ala
                405                 410                 415
Val Ile Asp Ile Leu Thr Leu Arg Lys Gln Thr Pro Leu His Leu Ala
            420                 425                 430
Ala Ala Ser Gly Gln Met Glu Val Cys Gln Leu Leu Leu Glu Leu Gly
        435                 440                 445
Ala Asn Ile Asp Ala Thr Asp Asp Leu Gly Gln Lys Pro Ile His Val
    450                 455                 460
Ala Ala Gln Asn Asn Tyr Ser Glu Val Ala Lys Leu Phe Leu Gln Gln
465                 470                 475                 480
His Pro Ser Leu Val Asn Ala Thr Ser Lys Asp Gly Asn Thr Cys Ala
                485                 490                 495
His Ile Ala Ala Met Gln Gly Ser Val Lys Val Ile Glu Glu Leu Met
            500                 505                 510
Lys Phe Asp Arg Ser Gly Val Ile Ser Ala Arg Asn Lys Leu Thr Asp
        515                 520                 525
Ala Thr Pro Leu Gln Leu Ala Ala Glu Gly Gly His Ala Asp Val Val
    530                 535                 540
Lys Ala Leu Val Arg Ala Gly Ala Ser Cys Thr Glu Glu Asn Lys Ala
545                 550                 555                 560
Gly Phe Thr Ala Val His Leu Ala Ala Gln Asn Gly His Gly Gln Val
                565                 570                 575
Leu Asp Val Leu Lys Ser Thr Asn Ser Leu Arg Ile Asn Ser Lys Lys
            580                 585                 590
Leu Gly Leu Thr Pro Leu His Val Ala Ala Tyr Tyr Gly Gln Ala Asp
        595                 600                 605
Thr Val Arg Glu Leu Leu Thr Ser Val Pro Ala Thr Val Lys Ser Glu
    610                 615                 620
Thr Pro Thr Gly Gln Ser Leu Phe Gly Asp Leu Gly Thr Glu Ser Gly
```

-continued

```
            625                 630                 635                 640
Met Thr Pro Leu His Leu Ala Ala Phe Ser Gly Asn Glu Asn Val Val
                    645                 650                 655
Arg Leu Leu Leu Asn Ser Ala Gly Val Gln Val Asp Ala Ala Thr Ile
                    660                 665                 670
Glu Asn Met His Gly His Ile Gln Met Val Glu Ile Leu Leu Gly Gln
                    675                 680                 685
Gly Ala Glu Ile Asn Ala Thr Asp Arg Asn Gly Trp Thr Pro Leu His
        690                 695                 700
Cys Ala Ala Lys Ala Gly His Leu Glu Val Val Lys Leu Leu Cys Glu
705                 710                 715                 720
Ala Gly Ala Ser Pro Lys Ser Glu Thr Asn Tyr Gly Cys Ala Ala Ile
                    725                 730                 735
Trp Phe Ala Ala Ser Glu Gly His Asn Glu Val Leu Arg Tyr Leu Met
                    740                 745                 750
Asn Lys Glu His Asp Thr Tyr Gly Leu Met Glu Asp Lys Arg Phe Val
                    755                 760                 765
Tyr Asn Leu Met Val Val Ser Lys Asn His Asn Asn Lys Pro Ile Gln
        770                 775                 780
Glu Phe Val Leu Val Ser Pro Ala Pro Val Asp Thr Ala Ala Lys Leu
785                 790                 795                 800
Ser Asn Ile Tyr Ile Val Leu Ser Thr Lys Lys Glu Arg Ala Lys Asp
                    805                 810                 815
Leu Val Ala Ala Gly Lys Gln Cys Glu Ala Met Ala Thr Glu Leu Leu
                    820                 825                 830
Ala Leu Ala Ala Gly Ser Asp Ser Ala Gly Lys Ile Leu Gln Ala Thr
                    835                 840                 845
Asp Lys Arg Asn Val Glu Phe Leu Asp Val Leu Ile Glu Asn Glu Gln
        850                 855                 860
Lys Glu Val Ile Ala His Thr Val Val Gln Arg Tyr Leu Gln Glu Leu
865                 870                 875                 880
Trp His Gly Ser Leu Thr Trp Ala Ser Trp Lys Ile Leu Leu Leu Leu
                    885                 890                 895
Val Ala Phe Ile Val Cys Pro Pro Val Trp Ile Gly Phe Thr Phe Pro
                    900                 905                 910
Met Gly His Lys Phe Asn Lys Val Pro Ile Ile Lys Phe Met Ser Tyr
                    915                 920                 925
Leu Thr Ser His Ile Tyr Leu Met Ile His Leu Ser Ile Val Gly Ile
        930                 935                 940
Thr Pro Ile Tyr Pro Val Leu Arg Leu Ser Leu Val Pro Tyr Trp Tyr
945                 950                 955                 960
Glu Val Gly Leu Leu Ile Trp Leu Ser Gly Leu Leu Leu Phe Glu Leu
                    965                 970                 975
Thr Asn Pro Ser Asp Lys Ser Gly Leu Gly Ser Ile Lys Val Leu Val
                    980                 985                 990
Leu Leu Leu Gly Met Ala Gly Val Gly Val His Val Ser Ala Phe Leu
                    995                1000                1005
Phe Val Ser Lys Glu Tyr Trp Pro Thr Leu Val Tyr Cys Arg Asn Gln
        1010                1015                1020
Cys Phe Ala Leu Ala Phe Leu Leu Ala Cys Val Gln Ile Leu Asp Phe
1025                1030                1035                1040
Leu Ser Phe His His Leu Phe Gly Pro Trp Ala Ile Ile Ile Gly Asp
                    1045                1050                1055
```

-continued

Leu Leu Lys Asp Leu Ala Arg Phe Leu Ala Val Leu Ala Ile Phe Val
            1060                1065                1070

Phe Gly Phe Ser Met His Ile Val Ala Leu Asn Gln Ser Phe Ala Asn
        1075                1080                1085

Phe Ser Pro Glu Asp Leu Arg Ser Phe Glu Lys Lys Asn Arg Asn Arg
    1090                1095                1100

Gly Tyr Phe Ser Asp Met Glu Gln Met Thr Cys Pro His Pro Asp Leu
1105                1110                1115                1120

Arg Arg Trp Arg Ile Met Ser Ile Val Ala Ser Ala Asn Ser Asp Glu
            1125                1130                1135

Ser Thr Arg Thr Thr Phe Pro Gly Gly Thr Ser Thr Ser Pro His Ser
        1140                1145                1150

Leu Leu Glu Ile Pro Ser Pro Cys Met His Val Asp Val Phe Ile Gln
        1155                1160                1165

Ser Ile Gln Thr Lys Ile Lys Gln Ser Ile Ser Asn Ile Asp Ile Thr
    1170                1175                1180

Asn Ala Arg Leu Pro Gly Ala Phe Ser Leu Arg Arg Leu Pro Thr Thr
1185                1190                1195                1200

Lys Phe Cys Thr Ile Glu Thr Ile Glu Thr Asp Arg Ile Glu Ser Ile
            1205                1210                1215

Thr Lys Asn Asp Asn Ala Thr Asp Thr Asp Tyr Arg Cys Ser Tyr Met
        1220                1225                1230

Leu Gly Pro Met Thr Pro Phe Leu Ala Phe Glu Arg Leu Phe Phe Ala
    1235                1240                1245

Val Phe Gly Gln Thr Thr Thr Leu Asp Ile Asn Pro Met Arg His Leu
    1250                1255                1260

Arg Pro Glu Trp Thr Glu Val Leu Phe Lys Phe Val Phe Gly Ile Tyr
1265                1270                1275                1280

Leu Leu Val Ser Val Val Leu Ile Asn Leu Leu Ile Ala Met Met
            1285                1290                1295

Ser Asp Thr Tyr Gln Arg Ile Gln Met Asn Arg Asn Trp Gly Leu Val
        1300                1305                1310

Asp Arg Thr Asn Gln Arg Asn Lys Lys Lys Lys Asn His Ile Ile
            1315                1320                1325

Glu Ser Thr Asn Pro Thr Trp Ala Ser Val Ile Phe Leu Phe Phe Lys
    1330                1335                1340

Ile Ile Ser Thr Pro Ala Asn Ile Cys Val Leu Ser Gly Gly Val Tyr
1345                1350                1355                1360

Leu Tyr Leu Tyr Leu Tyr Leu Glu Met Tyr Leu Trp Val Ser Asp Thr
            1365                1370                1375

Val Arg Met His Pro Ile Asn Ser Phe Glu Leu Leu Phe Phe Ala Val
        1380                1385                1390

Phe Gly Gln Thr Thr Thr Glu Gln Thr Gln Val Asp Lys Ile Lys Asn
    1395                1400                1405

Val Ala Thr Pro Thr Gln Pro Tyr Trp Val Glu Tyr Leu Phe Lys Ile
    1410                1415                1420

Val Phe Gly Ile Tyr Met Leu Val Ser Val Val Leu Ile Asn Leu
1425                1430                1435                1440

Leu Ile Ala Met Met Ser Asp Thr Tyr Gln Arg Ile Gln Ala Gln Ser
            1445                1450                1455

Asp Ile Glu Trp Lys Phe Gly Leu Ser Lys Leu Ile Arg Asn Met His
        1460                1465                1470

```
Arg Thr Thr Thr Ala Pro Ser Pro Leu Asn Leu Val Thr Thr Trp Phe
    1475                1480                1485
Met Trp Ile Val Glu Lys Val Lys Val Lys Ser Gln Val Thr Lys Val
1490                1495                1500
Ala Phe Gln Pro Leu Ser Leu Cys Leu Ser Leu Ser Ile Arg Ile Leu
1505                1510                1515                1520
Tyr Pro Val Ser Tyr Thr Cys Phe His Ile Cys Met Lys Lys Lys
            1525                1530                1535
Arg Pro Ser Leu Val Gln Met Met Gly Ile Arg Gln Ala Ser Pro Arg
        1540                1545                1550
Thr Lys Ala Gly Ala Lys Trp Leu Ser Lys Ile Lys Lys Ser Val Ala
    1555                1560                1565
Leu Ser Gln Val His Leu Ser Pro Leu Gly Ser Gln Ala Ser Phe Ser
1570                1575                1580
Gln Ala Asn Gln Asn Arg Ile Glu Asn Val Ala Asp Trp Glu Ala Ile
1585                1590                1595                1600
Ala Lys Lys Tyr Arg Ala Leu Val Gly Asp Glu Gly Gly Ser Leu
            1605                1610                1615
Lys Asp Ser Asp Ala Glu Ser Gly Ser Gln Glu Gly Ser Gly Gly Gln
        1620                1625                1630
Gln Pro Pro Ala Gln Val Gly Arg Arg Ala Ile Lys Ala Thr Leu Ala
    1635                1640                1645
Asp Thr Thr Lys Ser Lys Leu His Leu Ser Leu Gln Thr Ile Leu Pro
1650                1655                1660
Asp Tyr Leu Tyr Leu Phe Ser Thr Ile Gln Ala Ser Val Leu Leu Cys
1665                1670                1675                1680
Thr Leu Gly Met Val Phe Ser Asp Ser Gly Thr His Phe Phe Trp Phe
            1685                1690                1695
Asn Trp Ser Met Gly Lys Ser Asp
        1700

<210> SEQ ID NO 3
<211> LENGTH: 6156
<212> TYPE: DNA
<213> ORGANISM: Drosophila melanogaster
<220> FEATURE:
<223> OTHER INFORMATION: nompC cDNA sequence

<400> SEQUENCE: 3
tttctcgtcg ctccgaaaaa aggcaaaata gtaggcaacc tgaaatccag agttgtagtt      60
ggggactctt ttggccaaaa tacaaggagg agaaaaatag aaaataataa aggggggcacc    120 gccgttaacg cacacgcaac cgaagccata aaggggctaa acatataaat ttgtgtagta    180
aaagtgaaga aagcgaaaga atcaaagtgg aataatagcg agtgtttttc ggtttgctag    240
tgtgtttctg agtcggagtt tgtgtgtgtg tgtttgtgtg attcctagtg tgtctgttgc    300
tgttgccaat gaaatgcaa attgttggta acaaatattg gtaaaatgcg gaggccgtag    360
gaatttgtgc aatgcgagtg cgaagtgaag gagcccgaaa ctatgcagct aaaaacccgc    420
catcctaccc cgcatcgaat caataataat acaataaccc aaacgtatta cacggataat    480
ggcagcataa accagttaac atccgacagt gtttccgcct aaccatcgag cacctagctc    540 atccccctg ccaccaaccc ttcgaaaaat ccccatgatc agcgccggat tgtggagcag    600
taactagcga ggcataccag gatgtcgcag ccgcgcggag ggcgtggcgg tgggcgtggc    660
ggcggagtgg gtcgcaaaac cccctcctcg ctgaccggcc caccgatga gtcggctacg    720
```

-continued

```
cccagcgaac gggctacgcc cgccagcaaa gcagactccg atcccaagga cgatagctcg      780
agcaatggcg acaagaagga tatggatctt tttccagccc caaagccgcc gagtgccggc      840
gcctccattc gggacacggc gaacaaggtg ctcggattgg ccatgaaaag cgagtggacg      900
cccatcgagg cggagctcaa gaagctggaa aagtatgtgg ccaatgtggg cgaggatggc      960
aatcacatac cgctggccgg cgttcacgac atgaataccg gcatgacgcc gctgatgtac     1020
gcaacgaagg acaataagac ggccataatg gatcgcatga ttgagctggg cgccgatgtg     1080
ggagcccgca ataatgataa ttataatgtg ctacatattg ccgcaatgta ttcgcgtgag     1140
gatgtcgtca aattgttgct aacaaaacgc ggcgtggatc ccttctccac cggtggctcg     1200
cgttcgcaaa ctgcggtgca tttggtgtcc agtcgacaaa ccggaactgc aactaatatc     1260
ctgcgcgctc tgctcgcggc agctggcaag gatattcgct tgaaagcgga cggccgtggc     1320
aaaataccat tgctcctggc cgtggagtcg ggcaaccagt ccatgtgcag ggagctcctg     1380
gctgcacaaa cagcagagca gctcaaggca acgacggcca atggagacac ggccttgcat     1440
ttggccgcca gacggcggga cgtggacatg gtccgcatcc tggttgatta cggaacgaat     1500
gtggacacgc agaatgggga gggccagacg ccacttcata tcgcggccgc cgaaggcgat     1560
gaggctctac tcaagtactt ctatggcgtg cgcgcctcag cgtccattgc ggacaatcaa     1620
gatcgcactc cgatgcactt ggccgccgag aatgggcacg cgcacgtcat cgagatactg     1680
gccgacaagt tcaaggcgag catcttcgag cgcaccaagg atggcagcac gctgatgcac     1740
attgcgtcac tcaacggtca tgctgagtgc gccacgatgc tcttcaagaa gggcgtctac     1800
ctccatatgc ccaacaagga tggagcccgg agtattcaca ccgccgccgc ctatggtcac     1860
acgggaatca tcaacaccct gctacagaag ggcgagaaag tggatgtgac caccaatgat     1920
aactatacag cactgcacat agccgtggaa tcggctaagc ccgccgttgt ggaaaccctg     1980
ctgggatttg gagcagatgt ccatgtccgt ggcggaaaac tacgtgagac cccgctgcac     2040
attgcggcac gagtgaagga tggagatagg tgtgccctca tgttgctgaa gtcgggagcc     2100
agtccaaatt tgaccacgga tgactgtctg accccgtgc atgtggcggc tcgtcatggc     2160
aatctggcca cgttgatgca actcctcgag gacgaaggag atccgctgta caaatcgaat     2220
actggagaga caccgctgca catggcctgt cgtgcttgcc acccggatat tgtgcgtcat     2280
ctcatcgaga cggtgaagga gaaacacggt ccggataagg ccaccaccta tataaactcg     2340
gtaaacgagg acggcgccac ggcgttgcat tacacctgcc aaatcaccaa ggaggaggtt     2400
aagattcccg aatccgacaa gcagatcgtt cggatgctcc tcgaaaatgg tgcggatgtc     2460
acgttgcaaa cgaaaactgc cttggagacc gctttccact actgcgccgt ggccggcaac     2520
aatgatgtgc tgatggagat gatctcacat atgaatccca cagacatcca aaaggccatg     2580
aaccggcaat catcggtggg ctggactcca ctgctgattg cttgccatcg agggcacatg     2640
gagctggtca ataatctact ggcgaatcac gctcgagtgg atgtcttcga tacgaaggga     2700
cgatctgcct tgcatttggc tgctgagcga ggatacctgc atgtgtgtga tgccctgctg     2760
accaataagg ctttttatta actccaagtcc cgcgtgggac gcactgcact acatctggca     2820
gccatgaatg gatttacgca tctggtgaaa ttcctgatca aggatcacaa tgcagttatc     2880
gatattctaa cgttgagaaa gcaaacgccg ctccatttgg cggcagccag cgggcagatg     2940
gaagtctgtc agctgctcct cgagctgggc gccaatatcg atgcgacgga cgatctgggc     3000
cagaagccaa tccacgtcgc cgcccagaac aactactctg aagtggccaa actcttcctg     3060
cagcagcatc catccctggt gaatgccacc agcaaggatg gaaacacatg tgcccacatt     3120
```

```
gccgccatgc agggatccgt caaggtgatc gaggagctga tgaagttcga tcgatcgggt    3180
gtgatttcgg cgcggaataa acttacggat gccacgcccc ttcagctggc cgccagggc    3240
ggacatgcgg atgtggtgaa ggctcttgtg agagctggtg cctcctgcac cgaagagaac    3300
aaggcgggat tcaccgccgt tcatctggcg gcacagaatg gacatggtca ggtcttggat    3360
gtgctgaaaa gcacaaactc actaaggatc aatagcaaaa agttgggtct gacgccgctt    3420
catgtggctg cctattacgg acaggcggat accgtgcggg aattgctgac cagtgttccc    3480
gccaccgtca gtcggaaac tccaacggga caaagtttat ttggggatct gggcacggag    3540
tccggaatga caccactaca cttggcggcc ttttccggca acgagaacgt ggtgcgactg    3600
ctcctcaact ctgcgggtgt tcaagtggat gcggcgacca tcgagaacgg ctataatcca    3660
ctccatttgg cttgcttcgg tggtcacatg tcagtggtcg gtttgctcct aagtcggtcg    3720
gcggaactcc tccaatcgca ggatcgtaac ggcaggacgg gcctgcatat cgccgccatg    3780
catggccaca tccagatggt ggagattctg ctcggccagg gcgcggagat caacgcaacc    3840
gatcggaacg gttggacgcc actgcattgt gctgccaaag ctggccactt ggaggtggtg    3900
aagttgctgt gcgaggcggg tgcctcgcca aaatcggaga ccaactacgg ttgcgccgcc    3960
atttggttcg ccgcctccga gggacacaac gaggtcctgc ggtatctgat gaacaaggag    4020
cacgacacct acgcctgat ggaggacaag cgattcgtgt acaacctgat ggtggtgtcc    4080
aagaaccaca caacaagcc cattcaggag tttgtcctgg tatcaccagc acccgtggat    4140
acagccgcca aactgtccaa catctacata gtactctcga caaggaaaa agagcgcgcc    4200
aaggatctgg tagcagctgg caaacagtgc gaggcaatgg ccacggagct cttggccctg    4260
gcagctgggt cagattccgc cggaaagatc cttcaagcca ccgataagcg aaacgtggag    4320
tttctcgacg ttctcattga aaatgagcag aaggaagtga ttgcccacac ggtagttcag    4380
cgatacttgc aagaactctg gcatggctcc ctgacgtggg catcctggaa aatccttctg    4440
ctgctcgtgg ccttcatagt ctgcccacca gtgtggattg gattcacatt cccgatgggt    4500
cacaagttca acaaggtgcc catcatcaag ttcatgtcgt acctaacctc tcacatttac    4560
ctcatgatcc acctgagcat cgtgggcata acgcccattt acccagtgct ccgattgagt    4620
ttggtgccct actggtacga ggtgggtctt ctcatctggc tgagtggatt gctccttttc    4680
gagctgacga atccgtcaga taaatcggga ctgggatcga taaaggtgct cgtgctgctg    4740
ctcggcatgg ccggagtggg tgtccatgtc tcagcatttc tattcgtctc caaggagtac    4800
tggccaactt tggtgtattg tcgaaatcag tgcttcgcgt tggccttcct gctggcctgt    4860
gtgcagatcc tcgactttt gtccttccac cacctattcg gtccctgggc catcatcatt    4920
ggggatctgc tgaaggatct ggctcggttt ttggccgtcc tggccatctt tgtgttttggc    4980
ttttccatgc acattgtggc cctgaatcag agctttgcca atttctcacc ggaggatctg    5040
cgcagcttcg agaagaagaa ccgaaataga ggctacttca gtgacgtgcg catgcatccg    5100
attaactcgt tcgagttgtt gttcttcgcc gtgttcggac aaacgacgac cgagcaaacg    5160
caagttgaca aaatcaaaaa tgtagccacg cccactcaac cgtattgggt tgagtacctg    5220
ttcaaaattg tctttggcat ttacatgttg gtgtcggtgg ttgtgctcat taacctgctg    5280
attgctatga tgtcagacac ctatcaacgc attcaggtag tattgctaaa tgcgcttta    5340
tctaactcga ctctatttat taactcgtac tttaaccata agtatataaa tttcatattg    5400
cattgtgtat taatcattct ctatttcagc ataagaagta aatttacata tgaagatgat    5460
```

-continued

```
ttatatttct tagatatata atagcggtag ttaggaagtg agctgttttg ggaacatatt    5520
gagaaaatag ttaattaatc tggagaactt ggcatgctct gtaaatccat caactgccca    5580
gacttgcatc ttccaggttt tttcaggaaa ataatgttag caatctgagg gatacaattt    5640
tgtgaaagtg tatctcaaag atggaagcct gccgccttct agtgtagtac agtgcagagt    5700
agctttagtg gattagccgc cttgaagtgt gccctgcttt tgtgaccagt gttgagcgag    5760
gccaaaccag aaagtgttgg ttaacgcatg cttacaaaac cttatatata gaaatcgttg    5820
ctgcatgctt atatgtctgt gtttgtcatt gtctaggact taagtctgaa gagatacacc    5880
aatatggtgg ttaggttttg tatggtaatt ttgtgattgc catccaaaac aggcctctga    5940
atttgtgtat ttctattatt aacaacctga tttttgcagc tcttaagtta cgtattaaca    6000
aagtaaaaac ctgtaaaatc cgaggcttct gttcacgaaa ctcatcccgt ttattccttt    6060
gttcttgttc tctcctatat catgtctcat ccatccaaca tcgcgcacct cgctaaccaa    6120
taataaactg aacaaaaaaa aaaaaaaaaa actcga                              6156
```

<210> SEQ ID NO 4
<211> LENGTH: 1619
<212> TYPE: PRT
<213> ORGANISM: Drosophila melanogaster
<220> FEATURE:
<223> OTHER INFORMATION: amino acid sequence derived from nompC cDNA
      sequence

<400> SEQUENCE: 4

```
Met Ser Gln Pro Arg Gly Gly Arg Gly Gly Arg Gly Gly Gly Val
  1               5                  10                  15

Gly Arg Lys Thr Pro Ser Ser Leu Thr Gly Pro Pro Asp Glu Ser Ala
             20                  25                  30

Thr Pro Ser Glu Arg Ala Thr Pro Ala Ser Lys Ala Asp Ser Asp Pro
         35                  40                  45

Lys Asp Asp Ser Ser Asn Gly Asp Lys Lys Asp Met Asp Leu Phe
     50                  55                  60

Pro Ala Pro Lys Pro Pro Ser Ala Gly Ala Ser Ile Arg Asp Thr Ala
 65                  70                  75                  80

Asn Lys Val Leu Gly Leu Ala Met Lys Ser Glu Trp Thr Pro Ile Glu
                 85                  90                  95

Ala Glu Leu Lys Lys Leu Glu Lys Tyr Val Ala Asn Val Gly Glu Asp
            100                 105                 110

Gly Asn His Ile Pro Leu Ala Gly Val His Asp Met Asn Thr Gly Met
        115                 120                 125

Thr Pro Leu Met Tyr Ala Thr Lys Asp Asn Lys Thr Ala Ile Met Asp
    130                 135                 140

Arg Met Ile Glu Leu Gly Ala Asp Val Gly Ala Arg Asn Asn Asp Asn
145                 150                 155                 160

Tyr Asn Val Leu His Ile Ala Ala Met Tyr Ser Arg Glu Asp Val Val
                165                 170                 175

Lys Leu Leu Leu Thr Lys Arg Gly Val Asp Pro Phe Ser Thr Gly Gly
            180                 185                 190

Ser Arg Ser Gln Thr Ala Val His Leu Val Ser Ser Arg Gln Thr Gly
        195                 200                 205

Thr Ala Thr Asn Ile Leu Arg Ala Leu Leu Ala Ala Gly Lys Asp
    210                 215                 220

Ile Arg Leu Lys Ala Asp Gly Arg Gly Lys Ile Pro Leu Leu Leu Ala
225                 230                 235                 240
```

```
Val Glu Ser Gly Asn Gln Ser Met Cys Arg Glu Leu Leu Ala Ala Gln
                245                 250                 255

Thr Ala Glu Gln Leu Lys Ala Thr Thr Ala Asn Gly Asp Thr Ala Leu
            260                 265                 270

His Leu Ala Ala Arg Arg Asp Val His Met Val Arg Ile Leu Val
        275                 280                 285

Asp Tyr Gly Thr Asn Val Asp Thr Gln Asn Gly Glu Gly Gln Thr Pro
    290                 295                 300

Leu His Ile Ala Ala Glu Gly Asp Glu Ala Leu Leu Lys Tyr Phe
305                 310                 315                 320

Tyr Gly Val Arg Ala Ser Ala Ser Ile Ala Asp Asn Gln Asp Arg Thr
                325                 330                 335

Pro Met His Leu Ala Ala Glu Asn Gly His Ala His Val Ile Glu Ile
            340                 345                 350

Leu Ala Asp Lys Phe Lys Ala Ser Ile Phe Glu Arg Thr Lys Asp Gly
        355                 360                 365

Ser Thr Leu Met His Ile Ala Ser Leu Asn Gly His Ala Glu Cys Ala
    370                 375                 380

Thr Met Leu Phe Lys Lys Gly Val Tyr Leu His Met Pro Asn Lys Asp
385                 390                 395                 400

Gly Ala Arg Ser Ile His Thr Ala Ala Tyr Gly His Thr Gly Ile
                405                 410                 415

Ile Asn Thr Leu Leu Gln Lys Gly Glu Lys Val Asp Val Thr Thr Asn
            420                 425                 430

Asp Asn Tyr Thr Ala Leu His Ile Ala Val Glu Ser Ala Lys Pro Ala
        435                 440                 445

Val Val Glu Thr Leu Leu Gly Phe Gly Ala Asp Val His Val Arg Gly
    450                 455                 460

Gly Lys Leu Arg Glu Thr Pro Leu His Ile Ala Ala Arg Val Lys Asp
465                 470                 475                 480

Gly Asp Arg Cys Ala Leu Met Leu Leu Lys Ser Gly Ala Ser Pro Asn
                485                 490                 495

Leu Thr Thr Asp Asp Cys Leu Thr Pro Val His Val Ala Ala Arg His
            500                 505                 510

Gly Asn Leu Ala Thr Leu Met Gln Leu Leu Glu Asp Glu Gly Asp Pro
        515                 520                 525

Leu Tyr Lys Ser Asn Thr Gly Glu Thr Pro Leu His Met Ala Cys Arg
    530                 535                 540

Ala Cys His Pro Asp Ile Val Arg His Leu Ile Glu Thr Val Lys Glu
545                 550                 555                 560

Lys His Gly Pro Asp Lys Ala Thr Thr Tyr Ile Asn Ser Val Asn Glu
                565                 570                 575

Asp Gly Ala Thr Ala Leu His Tyr Thr Cys Gln Ile Thr Lys Glu Glu
            580                 585                 590

Val Lys Ile Pro Glu Ser Asp Lys Gln Ile Val Arg Met Leu Leu Glu
        595                 600                 605

Asn Gly Ala Asp Val Thr Leu Gln Thr Lys Thr Ala Leu Glu Thr Ala
    610                 615                 620

Phe His Tyr Cys Ala Val Ala Gly Asn Asn Asp Val Leu Met Glu Met
625                 630                 635                 640

Ile Ser His Met Asn Pro Thr Asp Ile Gln Lys Ala Met Asn Arg Gln
                645                 650                 655
```

```
Ser Ser Val Gly Trp Thr Pro Leu Leu Ile Ala Cys His Arg Gly His
            660                 665                 670

Met Glu Leu Val Asn Asn Leu Leu Ala Asn His Ala Arg Val Asp Val
            675                 680                 685

Phe Asp Thr Glu Gly Arg Ser Ala Leu His Leu Ala Ala Glu Arg Gly
            690                 695                 700

Tyr Leu His Val Cys Asp Ala Leu Leu Thr Asn Lys Ala Phe Ile Asn
705                 710                 715                 720

Ser Lys Ser Arg Val Gly Arg Thr Ala Leu His Leu Ala Ala Met Asn
                725                 730                 735

Gly Phe Thr His Leu Val Lys Phe Leu Ile Lys Asp His Asn Ala Val
            740                 745                 750

Ile Asp Ile Leu Thr Leu Arg Lys Gln Thr Pro Leu His Leu Ala Ala
            755                 760                 765

Ala Ser Gly Gln Met Glu Val Cys Gln Leu Leu Leu Glu Leu Gly Ala
            770                 775                 780

Asn Ile Asp Ala Thr Asp Leu Gly Gln Lys Pro Ile His Val Ala
785                 790                 795                 800

Ala Gln Asn Asn Tyr Ser Glu Val Ala Lys Leu Phe Leu Gln Gln His
                805                 810                 815

Pro Ser Leu Val Asn Ala Thr Ser Lys Asp Gly Asn Thr Cys Ala His
            820                 825                 830

Ile Ala Ala Met Gln Gly Ser Val Lys Val Ile Glu Glu Leu Met Lys
            835                 840                 845

Phe Asp Arg Ser Gly Val Ile Ser Ala Arg Asn Lys Leu Thr Asp Ala
850                 855                 860

Thr Pro Leu Gln Leu Ala Ala Glu Gly Gly His Ala Asp Val Val Lys
865                 870                 875                 880

Ala Leu Val Arg Ala Gly Ala Ser Cys Thr Glu Glu Asn Lys Ala Gly
                885                 890                 895

Phe Thr Ala Val His Leu Ala Ala Gln Asn Gly His Gly Gln Val Leu
            900                 905                 910

Asp Val Leu Lys Ser Thr Asn Ser Leu Arg Ile Asn Ser Lys Lys Leu
            915                 920                 925

Gly Leu Thr Pro Leu His Val Ala Ala Tyr Tyr Gly Gln Ala Asp Thr
            930                 935                 940

Val Arg Glu Leu Leu Thr Ser Val Pro Ala Thr Val Lys Ser Glu Thr
945                 950                 955                 960

Pro Thr Gly Gln Ser Leu Phe Gly Asp Leu Gly Thr Glu Ser Gly Met
                965                 970                 975

Thr Pro Leu His Leu Ala Ala Phe Ser Gly Asn Glu Asn Val Val Arg
            980                 985                 990

Leu Leu Leu Asn Ser Ala Gly Val Gln Val Asp Ala Ala Thr Ile Glu
            995                 1000                1005

Asn Gly Tyr Asn Pro Leu His Leu Ala Cys Phe Gly Gly His Met Ser
   1010                 1015                 1020

Val Val Gly Leu Leu Leu Ser Arg Ser Ala Glu Leu Leu Gln Ser Gln
1025                1030                 1035                1040

Asp Arg Asn Gly Arg Thr Gly Leu His Ile Ala Ala Met His Gly His
                1045                1050                1055

Ile Gln Met Val Glu Ile Leu Leu Gly Gln Gly Ala Glu Ile Asn Ala
            1060                1065                1070

Thr Asp Arg Asn Gly Trp Thr Pro Leu His Cys Ala Ala Lys Ala Gly
```

```
                1075                1080                1085
His Leu Glu Val Val Lys Leu Leu Cys Glu Ala Gly Ala Ser Pro Lys
    1090                1095                1100
Ser Glu Thr Asn Tyr Gly Cys Ala Ala Ile Trp Phe Ala Ala Ser Glu
1105                1110                1115                1120
Gly His Asn Glu Val Leu Arg Tyr Leu Met Asn Lys Glu His Asp Thr
            1125                1130                1135
Tyr Gly Leu Met Glu Asp Lys Arg Phe Val Tyr Asn Leu Met Val Val
        1140                1145                1150
Ser Lys Asn His Asn Asn Lys Pro Ile Gln Glu Phe Val Leu Val Ser
    1155                1160                1165
Pro Ala Pro Val Asp Thr Ala Ala Lys Leu Ser Asn Ile Tyr Ile Val
1170                1175                1180
Leu Ser Thr Lys Glu Lys Glu Arg Ala Lys Asp Leu Val Ala Ala Gly
    1185                1190                1195                1200
Lys Gln Cys Glu Ala Met Ala Thr Glu Leu Leu Ala Leu Ala Ala Gly
            1205                1210                1215
Ser Asp Ser Ala Gly Lys Ile Leu Gln Ala Thr Asp Lys Arg Asn Val
        1220                1225                1230
Glu Phe Leu Asp Val Leu Ile Glu Asn Glu Gln Lys Glu Val Ile Ala
    1235                1240                1245
His Thr Val Gln Arg Tyr Leu Gln Glu Leu Trp His Gly Ser Leu
    1250                1255                1260
Thr Trp Ala Ser Trp Lys Ile Leu Leu Leu Val Ala Phe Ile Val
1265                1270                1275                1280
Cys Pro Pro Val Trp Ile Gly Phe Thr Phe Pro Met Gly His Lys Phe
            1285                1290                1295
Asn Lys Val Pro Ile Ile Lys Phe Met Ser Tyr Leu Thr Ser His Ile
        1300                1305                1310
Tyr Leu Met Ile His Leu Ser Ile Val Gly Ile Thr Pro Ile Tyr Pro
    1315                1320                1325
Val Leu Arg Leu Ser Leu Val Pro Tyr Trp Tyr Glu Val Gly Leu Leu
    1330                1335                1340
Ile Trp Leu Ser Gly Leu Leu Leu Phe Glu Leu Thr Asn Pro Ser Asp
1345                1350                1355                1360
Lys Ser Gly Leu Gly Ser Ile Lys Val Leu Val Leu Leu Leu Gly Met
            1365                1370                1375
Ala Gly Val Gly Val His Val Ser Ala Phe Leu Phe Val Ser Lys Glu
            1380                1385                1390
Tyr Trp Pro Thr Leu Val Tyr Cys Arg Asn Gln Cys Phe Ala Leu Ala
    1395                1400                1405
Phe Leu Leu Ala Cys Val Gln Ile Leu Asp Phe Leu Ser Phe His His
    1410                1415                1420
Leu Phe Gly Pro Trp Ala Ile Ile Ile Gly Asp Leu Leu Lys Asp Leu
1425                1430                1435                1440
Ala Arg Phe Leu Ala Val Leu Ala Ile Phe Val Phe Gly Phe Ser Met
            1445                1450                1455
His Ile Val Ala Leu Asn Gln Ser Phe Ala Asn Phe Ser Pro Glu Asp
            1460                1465                1470
Leu Arg Ser Phe Glu Lys Lys Asn Arg Asn Arg Gly Tyr Phe Ser Asp
        1475                1480                1485
Val Arg Met His Pro Ile Asn Ser Phe Glu Leu Leu Phe Phe Ala Val
    1490                1495                1500
```

Phe Gly Gln Thr Thr Thr Glu Gln Thr Gln Val Asp Lys Ile Lys Asn
1505                1510                1515                1520

Val Ala Thr Pro Thr Gln Pro Tyr Trp Val Glu Tyr Leu Phe Lys Ile
            1525                1530                1535

Val Phe Gly Ile Tyr Met Leu Val Ser Val Val Leu Ile Asn Leu
        1540                1545                1550

Leu Ile Ala Met Met Ser Asp Thr Tyr Gln Arg Ile Gln Val Val Leu
        1555                1560                1565

Leu Asn Ala Leu Leu Ser Asn Ser Thr Leu Phe Ile Asn Ser Tyr Phe
    1570                1575                1580

Asn His Lys Tyr Ile Asn Phe Ile Leu His Cys Val Leu Ile Ile Leu
1585                1590                1595                1600

Tyr Phe Ser Ile Arg Ser Lys Phe Thr Tyr Glu Asp Asp Leu Tyr Phe
            1605                1610                1615

Leu Asp Ile

<210> SEQ ID NO 5
<211> LENGTH: 9758
<212> TYPE: DNA
<213> ORGANISM: Caenorhabditis elegans
<220> FEATURE:
<223> OTHER INFORMATION: nompC genomic nucleotide sequence

<400> SEQUENCE: 5

```
ctttgccgct taaaattttg cagtgacata tccttatgga acactttcaa atgacacatg    60
tctcgtttta aagtctgacg gtaaactaaa acatttcct tgtaagccta aacctaagcc   120
aaagcctaag cctaataagc ctagctaacg ctcgccactg acgccaagcc taagactaat   180
cctacgccaa tgcctaaaac tgacactgaa ataaaagtca aaagccaaaa gccaaaagcc   240
aaaacctaag gccgaagcat aaggccaaag cctatgccta agcctgagcc tgagcttaaa   300
tcctaagcct aagcctaagg ccaaagaaca agcctaagtc taagtccaag cctaagtatc   360
aaaaacttac accgattccg ccaggctacc ctcagcacaa ttatcaactt tgttaacata   420
tttatcggcg acggcgtggc gcttttctta ttcatctgtc tgatcagaat agctcttccg   480
aacttccatt ccttatccga ctgtgcctga attcgttggt aggtgtcaga catcatagca   540
atcagcaagt tgatcagcac aatcaaggtg accatcatgt agattccgaa tagaagtttt   600
aagatgattt ttgcaaaatc tggaactaga tggagcgggg gcattgaatc gggctcgacg   660
agtccgaaga gcgagaagaa gagcatttcg agggtttgag acggggaggc cagacgcatc   720
agctcggcgc tgtcctcgtc gacaggctgg taggcaggct gaaaaaatct ctttcaaggc   780
tcgttttct tgcctaacct acctggaaga tactcgtcac gtggagtgtg aagcccgcca    840
cgaacaacat caggatcaca aggaaacggg ccaaatcata cattagatcg ctgaaagctt   900
cttcttctaa ggggtcagct caagccaagt actcaccgaa taatgatcgc ccagggaccg   960
aacaaatgat gcactgtcag gaaatccagg tactctacaa aagcaaatag cagggcaaag   1020
gcgaaaagtt gattttcaa ataaagcatt gtccgggcga aatgtagctt ttcatcgtta   1080
tccaggtggg ttaggaatac tgccgggagc aggaaggcta ggacatggac ggctatcgcc   1140
atcgcggaaa ggactaggat taggaccttt acgattccta ggccagatcc tccaccgaca   1200
gtggagagtt cggagaccag atttccagag agccagagca acaggagcca ttccacaggg   1260
tttggaacca ccgaagttac ttcgtacctg gaaattgaga ttttgcaggt ctatctgata   1320
tccctaaat aaaatttaaa aaaataactt acatcttatg tgtaatattc aacaccacaa    1380
```

```
ttgtcagcag tatcgtaaaa tagacatgag acacgatatg gcacacaaat ttaataatcg    1440
gagctcttcc gatccgacta tccagtggaa gtgagaagta gaaccatgcc gggggggcata   1500
ttagcacgaa gagggagaat gcgacaaact ttccgaatga ccagtcgaca cgggcagtcc    1560
atacttctgt caggtagcgt tggacagacg cgtaggagac tacttctttc tggaaacggg    1620
gtcgttgagg gttgactggt taggttaagc ttggagtgtt acctgctcat tttcaatgag    1680
aacatctagt aggggccggc ctcgattgtc cttagccttc aggagaagag cggcattgta    1740
ttcggtggcg gtgatccctg aaataatcta ggactagtaa attgtaagtc attttctgaa    1800
aagattaaat agctaagtgg acctgtagcc ttggccggta actttggtcc aataaccttg    1860
gtccagtaac cttaatcctg taaaccttgg tcctgaaatc ttggcctagt aacctaaaac    1920
cttggtcctg tggtcctgac cctgttcctg tatccttggt tgggaaaccc tagtccttgt    1980
cctggtttgg aaaccctggc ccggtagcct tggtccaggt actggtcctg tgcccttggt    2040
cctggttctg gtcttggtcc cgaaaccttg gtccggcagt tttggttctg gtaccttggt    2100
cgtgtaacct taaacccagt aaccttggac cggtaacctt ggtacagtaa ctttggtccg    2160
gaagccctgg ctcggtaact ctggtcctgg tcatggtgtt ggtcctggcc cggacaccct    2220
ggtccggtaa ccctggtcta gcaaccttgg tcttgaccta caaccttggt ttctgtaacc    2280
ttggtcttgt aacttcggcc ctgtatcctt ggcccaaaga ccttggtccg acagccttgg    2340
ttctgatacc ttggtccagt aactttggtc gtggtcctgg ttcaggtcca gtaaccttga    2400
cccgataatc ctggtcttac ctagtgacct tggcccggta atcctgatcc tggcccagta    2460
accttggtcc agtacggtgg ccctgcaact atggcctagt agctttggtc cagtagccct    2520
gatcccgaaa ccttggttca gtaaccttgg tcttggtcca gtaactttgg tctagtaacc    2580
atagtccagt aaccctggtc ctgtaacctt ggtccgctag ccccgttagt catgttcccg    2640
ctcctggtcc ggcagcattg gtccggtaat tttggacctc ccctgggcct tggcccaggg    2700
catgttcctg gtccagggggg ccatttcctt cgttttttcat tacctaccta acaactccac   2760
agccatattc tcactgaaca ctgccacatt caacagatcc ttcgccctct ccttctcctt    2820
ctccgacata tctctgtaca acgcggacaa cttgactgcc gtctcaattg gagcaggtga    2880
ttgaagaata aactcttgta gaggctcatt gtcattggtt ttaccacaaa ccatcaagtc    2940
gaatatgaac ttccgatctt ccatcaattg atgtgtgtca tgcttctgtt tcaggaggaa    3000
tcgaagacat tctatatgat tatgagctgc agcaaagcac aatggaactt tgccctcctt    3060
ggtctccgcc aatggatccg ctgaactatc gatgaacagc ttgacgacac tcaggtgccc    3120
ggcacgagtg gcaaagtgaa gaccagtcca gccattctga tccatgacat tgatgttaga    3180
tccctgagca atgagaagtg agaccatctc gtagtggcca ttctgagcgg ctaggtggag    3240
cggggtcctg cctctccaat ccttggcgtg ctgctgctga gtagatctgg acaggagcat    3300
tcctaccact gcgatgtggc cttgctgggc agccagatgg agggggatca cgttctgaaa    3360
cggaattttta aacggggtca ctgaaaattt caagttacca ttgtagtact ggtcgcgtca    3420
acttgcactc cctgattcag aagcatccgc acaagactgt cgtgtccact atgagcggct    3480
aaatggagag gtgtgaagcc gtattcagtt gagaattcct tattgacatg gtgattgtag    3540
atgggcggct cggaacggac tgttgcttgt acgtgcttga gcatttcatt gacgaaatcc    3600
gaatttccgt agaacgcagc gatgtggaga gcgttgagac cggtctggaa atgctaggtt    3660
cagggggaat cgagttttttt ttcagtacaa aattcataaa atttaaggct agctgtgaaa    3720
```

```
aattgtgcta ccaaagtata ggccacggct tcaaatttga caggacttat tccactttgc   3780
agatcagacc tttatgcatg aactgtactg ccacgtattg gaaaatgtta tttttgacag   3840
ccttaccttt ctcgaacacc gtttccatag gatcttatcg aatgcctcca aaatcgatat   3900
gaatccgttt ttggcgccaa ggtggagagc agtcattccg tgctgaaaat caattctgcc   3960
taaaaatcgg taaagaacc cctaccgaat tctcatcttc cgcgtttgct ccattctcca   4020
gcagaatctt cacaatgttc gcgtgacctc ccgcagctgc catatgaagt gtagtggctt   4080
ccagtgtttt ggtctttgcc tggattacca taggcttgtc gatcatcata agctcacgga   4140
ccacggctag ggaaccctgg aacaatatta ttttagttgc aatcaaaagc tgaagcttcc   4200
accccatacct tcatcgcagc aatatgtgcg caggtgaatc cattatgatc aattgcggtc   4260
aacacactcc ggttgttatt tctcattttc aggaagagct tcacaacgtc ggggaagtca   4320
ttctcagctg ccagatggag aggggtttga cccttgtcgt cacgtgcatt ggggtttgct   4380
ccgagagcca aagggtttg actcacagct agctgaccga attttgcggc aaagtggagg   4440
gctgtctgga aattatttgt gtttctaatc aggagcttgc cgacaaattt gctcgaaccc   4500
cgtattagaa actacgcaga accctgtctg ggcagtagat tacctctagc ttggatacta   4560
tcttacctga ttatccagcg taattgcctc cagcgctgca ccatgatcct gcaccaggac   4620
attcaccacc ttcacatgac catgctgagc tgctaagtgg agcggtgcct ctccggtttt   4680
cgatttactg ttcacgaatg ctttgtgctg cagaagaagg tgaaccaggg agagatgccc   4740
attgaaagct gccaggtgca gagcagtacg gcccatttca tcgaatacat caatacgggc   4800
gtggtgctga aaaagtatga ggtatccggt ttgtgagaaa tcagtggtcc cccagtagcc   4860
ttggcacagt aaccttggtc ctggtcctgg tcctcgccca gtaaccctgg tcctgtaacc   4920
ctggtcctgt agccctggcc ctggtcctgg tcctggtcct gcccagtaa ccttggtact   4980
gtaaccatgg tactgtaacc ctggccctgg tcctggtcca gtaacctcgg ccctgtaacc   5040
ttggtcctgg tcctggtcct ggtcctacac acaaaaccag taccttcaac aaaatattcg   5100
ccactccaga atgccctctg gcacatgctt ccaacagcgg tgaccatccg ttcttgctct   5160
gcttgttctg cacgatttgc accgcaccgg ctccgatctt attgaccatc gccaggagta   5220
cagcttgatt tccggatctt gccgccatat gcatcgccgt ctcatttgca ttgagtgatg   5280
gcatttctac cattccaccg tagtcgatca gaagatttac tagcttggca tcttctcctg   5340
gaaagtgtaa ctggcgctgc tcgatttcag cggcgtagtg aagagctgtg aagccgtcct   5400
gaaaaattta acttgaagct tcctgagatc cagagaaaga agctcacatt ggttctatga   5460
ttgacatgtt ccttaagctg ttcttgggtc agaacttccg aaaggtgctt caaaatcatt   5520
gatgctgctt caaaattgca tgacttggcg gccacctgga ggggtgtctc tccgatcttt   5580
gagcttattt tcgagtcggc gttctcgtca agcaggagcc tggaaaaaag gaggttcttg   5640
ggcttttaca ggatccgaca gaaaatagat ttctcgaact ttttcccgtt ttcgtactgt   5700
caatttacca aatttcaagg taccctgttt ttataagtgc ttagaaattt caaaaatttc   5760
aaaaattgtg ataaactggg gcgctgaatc cagaattggc acagaaattc agagtttctc   5820
aattttcaaa gaggcttgta tgcaatgctt agaaatccta aattttgagc acgcagttca   5880
cgggctccag gaccaagtgc acaataatct caaaattttt gggtcccaca gcagttgcgc   5940
gctagctgaa aaattctgca cggcatgaga agtggcacct gtacgcaatt tgtctaccgt   6000
atacctggac gtttagtagc gttttttca aatttttg gaccaaagct ttttcctca   6060
aaacgcgcct aaacgtggct aaaactgcaat tatcagttga gcgcgtttac actgatatac   6120
```

```
actttgcagg gccgtgtgct gattggctct aaagtcggcg tggctaagca ctgattagtc   6180
aagatcacct acttacctca tgatatcctt attcccactc ctggcagcaa tatgcagaca   6240
agtctcccca tccatttgtg caacatccgg ctgccctcca cttttcagca acatcatcgc   6300
acaatcccga ctctcggctc cattcaagct tgccgcaatg tgcagtgcag tttgtcctaa   6360
aaccaatctt ccatgaaatc ttattaatct cttattaatt taatacctag ttccccgccc   6420
ttcacatgaa tgtctgcacc acttcccagc agggtctcta caaccgaagc cttgccagat   6480
tgaaccgcta cgtggagagc ggtgtagttg tctcgtgtac ggacatctac attagtaccc   6540
cgagcaatga gcattttgac gacgtcgttg aagccagcag ctgctgcgga gtgaagaccc   6600
agggctcctt ttttgttggg catgaagagg gggactcctg gaagttagaa ttaacaatgt   6660
aagtcgaggg ggtgctgaga ccctgtaaac ctacctctct tcaaaaacgc caatgcggtg   6720
ctagtatgtc ctgaacatgc ggcaatatgc agaagcgtcg acccatcacg ggtcctagcg   6780
cgaattgagc caccaaactt gtcaattagt gactcgacca tcgaagtgtc acctcgctcc   6840
gctgcaacgt gtaccggagt cttgtcctcc ttatcatgga tgttggcgtc ggcgcggagt   6900
ttgaacatga tttttagcat attttgatct ccgacttcgg ctacctggaa aattggagat   6960
agagatactg tatgtgtgca gaggcataaa ttcagatagg agtagtacca agctttgatg   7020
gagcatgaat ctagttaagg tgtatcaggg atactgtaaa ggtacggtag tccggcatat   7080
tgtatttctg acaaatctac tgtattgggt acagtaagct cagtaaccct tctgtgtacc   7140
cgttacagtg aggcaagcta aacttaggcc attttttcctg ttaaaaaacc catttaaatg   7200
ttgcctagat cagaacaagc ctcgaatttt acagcttcat cagcaaaatt tcagcttcag   7260
gagctactta aagtttcaat ttccacccct taacctacct catgtagcgg cgtccttccc   7320
accctattct gcacattcgc attatcacat ccagccgcaa tcgctgtccg aaccgcttcg   7380
atattcccac tccgagcggc caaatgaagc aaggtatccc cgtttccatc agctttcctg   7440
gtttgttcat ccgaaggccc acttagcaga agctccacaa tattaacatt cccaaacttg   7500
aatgccaagt gtatcggcaa ggatccatcc ccatcctctg ccattctttg atcagtatct   7560
tccaaaatcc gcttcacaat tggaaatgct ttcttggatt ttctctcgca agccacatgg   7620
attgccagct gcttttttagg ccccgcacct tttcggagca gctcagagta tcgcttgagg   7680
ataagctcaa gagtttcaac tccggagtac atggcggcaa tatgagtcgc gttacggcca   7740
tctttagtgc tatagtccac tcgagcacct tttcggatca tcttgtctac gatttgatcc   7800
ttgccagctt tgacggctag gaggaaggcg gtgaagccgt gctgcaagga gaattttttag   7860 aaaatggcgg gtacaatcta aagtgaaaat ctaagtcagt ttcggggaat tttgggttag   7920
ggctgctaaa cggctgcgag gggctcagca cattgaaaaa cgcagtgcta tatgtagttg   7980
ttttgcagcc ccgggggttcc gcaggcctca cgccactagc caccatggtc ctatgtatag   8040
tgccgtgcgg aaccccgaaa gtgtcggcgg ctgccaaaca tctgcctatt gcactgcatt   8100
gtccaatgcg aaggctcaac cccactgaag gtactacccc ctaatagtca gcagccctaa   8160
tttgggtcaa accctaaaat tgcgaacttc accgacttgt ccgagttaca gcggaaaaaa   8220
cttacattat cagccatact aaaatcactc cgcttgatag tctctatctc agactccaca   8280
ttcgcccact catctctctt cgcgaaatac aaaatcttcg tctgaggatc cgccattgcc   8340
aagtcctcac tcgacatttc ctcatgagac gatgcgtggg aggtgagact ctctcgaaac   8400
agaggtttcc cgagaagacg atccggcggg gtgactgaat cacgggatgg ttgtttcgga   8460
```

-continued

```
acgaagatga tccgtgagtt ctttccgatt tggagatggg tcgaggatcg gcggaggggt    8520
ggtcggtcag ttgggatggt gtcggtggtg aggaggtcct ggaaagtggg tagaattagt    8580
tttcgtaagc ttccaggcgt gcctacacgc cttcctgttg cctacgaaaa gtcctgaatc    8640
taaaaagcat ttttggcagc atccatctaa aaaaatcggt atctttgagt agttttaaac    8700
agtgttcttc cacgaaaaaa gttttccacg tcttgcctaa gtaagcctaa gcctcagctt    8760
aagcctaagc atatgcctaa gctaaatcct aagcctaagc ctgagtctga gcctgagcct    8820
aagcctattc caaagcttaa accgaagctt aagtctaggc cttagcctaa acctaagcct    8880
aaacctaagc ctaagcctaa gcctaagcct caacctaagc ctaaacctaa acctaatcaa    8940
atgcctacct ttttcccggt aaaccactcg gcccgtgtca ccgacgtcga gcgggtttcc    9000
cgtttccgca cagttagaca ttttccgat cttgacattt tcagtattac agaacagaa    9060 aaagaaggga aataataca tttctctcaa ctaattgggg ggcggacgca catggtgtcc    9120
tccaacccat aaaaaagtac gaatgtgggc gattaattgc gaaaaatgcg cgaaattat    9180 ttacgactga cgacgagaag cattaaactt tggtaaagg gtgctgtggg ggtactttgg    9240
tgaaaatata gctaaaattt aggcttgggc ttgggcttag gcttaggctt aggtttcagc    9300
tcaggcttag gcttcggctc aggctttggc gtaggcttaa actttggctt aggtttaagc    9360
ttaggcttag gctaggcttt agtcttaggc ttaggcttag gcttaggctt aggctcaggt    9420
ttaagcttag acttaggctc aggtttaggc ttggcgtcag tggcgagcgt tactgaagtg    9480
atatttaatc actctgatga tatttaattc cgatgattaa tccactttc ttttctcac    9540 atttatgaac caagttctaa attaaggtgg gatattttaa ggtgtgttaa catatgatat    9600 ttattttta atttaaatat agtttctctt tttgcttctt tttataagtt ttgttaatga    9660
acgcatagtt tacaaccgcc tcgctcaaat gtattttgat aaaagtgcgc tattaggctt    9720
aagcgtcgcc ataccgccgg tgtggtcata aggaattc                            9758
```

<210> SEQ ID NO 6
<211> LENGTH: 1709
<212> TYPE: PRT
<213> ORGANISM: Caenorhabditis elegans
<220> FEATURE:
<223> OTHER INFORMATION: amino acid sequence derived from nompC genomic
      sequence

<400> SEQUENCE: 6

```
Met Ser Arg Ser Glu Lys Cys Leu Thr Val Arg Lys Arg Glu Thr Arg
  1               5                  10                  15

Ser Thr Ser Val Thr Arg Ala Glu Trp Phe Thr Gly Lys Lys Met Asp
             20                  25                  30

Ala Ala Lys Asn Ala Phe Asp Leu Leu Thr Thr Asp Thr Ile Pro Thr
         35                  40                  45

Asp Arg Pro Pro Leu Arg Arg Ser Ser Thr His Leu Gln Ile Gly Lys
     50                  55                  60

Asn Ser Arg Ile Ile Phe Val Pro Lys Gln Pro Ser Arg Asp Ser Val
 65                  70                  75                  80

Thr Pro Pro Asp Arg Leu Leu Gly Lys Pro Leu Phe Arg Glu Ser Leu
                 85                  90                  95

Thr Ser His Ala Ser Ser His Glu Glu Met Ser Ser Glu Asp Leu Ala
            100                 105                 110

Met Ala Asp Pro Gln Thr Lys Ile Leu Tyr Phe Ala Lys Arg Asp Glu
        115                 120                 125
```

-continued

```
Trp Ala Asn Val Glu Ser Glu Ile Glu Thr Ile Lys Arg Ser Asp Phe
            130                 135                 140

Ser Met Ala Asp Asn His Gly Phe Thr Ala Phe Leu Leu Ala Val Lys
145                 150                 155                 160

Ala Gly Lys Asp Gln Ile Val Asp Lys Met Ile Arg Lys Gly Ala Arg
                165                 170                 175

Val Asp Tyr Ser Thr Lys Asp Gly Arg Asn Ala Thr His Ile Ala Ala
            180                 185                 190

Met Tyr Ser Gly Val Glu Thr Leu Glu Leu Ile Leu Lys Arg Tyr Ser
        195                 200                 205

Glu Leu Leu Arg Lys Gly Ala Gly Pro Lys Lys Gln Leu Ala Ile His
    210                 215                 220

Val Ala Cys Glu Arg Lys Ser Lys Lys Ala Phe Pro Ile Val Lys Arg
225                 230                 235                 240

Ile Leu Glu Asp Thr Asp Gln Arg Met Ala Glu Asp Gly Asp Gly Ser
                245                 250                 255

Leu Pro Ile His Leu Ala Phe Lys Phe Gly Asn Val Asn Ile Val Glu
            260                 265                 270

Leu Leu Leu Ser Gly Pro Ser Asp Glu Gln Thr Arg Lys Ala Asp Gly
        275                 280                 285

Asn Gly Asp Thr Leu Leu His Leu Ala Ala Arg Ser Gly Asn Ile Glu
    290                 295                 300

Ala Val Arg Thr Ala Ile Ala Ala Gly Cys Asp Asn Ala Asn Val Gln
305                 310                 315                 320

Asn Arg Val Gly Arg Thr Pro Leu His Glu Cys Leu Thr Val Thr Gly
                325                 330                 335

Thr Gln Lys Gly Tyr Val Ala Glu Val Gly Asp Gln Asn Met Leu Lys
            340                 345                 350

Ile Met Phe Lys Leu Arg Ala Asp Ala Asn Ile His Asp Lys Glu Asp
        355                 360                 365

Lys Thr Pro Val His Val Ala Ala Glu Arg Gly Asp Thr Ser Met Val
    370                 375                 380

Glu Ser Leu Ile Asp Lys Phe Gly Gly Ser Ile Arg Ala Arg Thr Arg
385                 390                 395                 400

Asp Gly Ser Thr Leu Leu His Ile Ala Ala Cys Ser Gly His Thr Ser
                405                 410                 415

Thr Ala Leu Ala Phe Leu Lys Arg Val Pro Leu Phe Met Pro Asn Lys
            420                 425                 430

Lys Gly Ala Leu Gly Leu His Ser Ala Ala Ala Gly Phe Asn Asp
        435                 440                 445

Val Val Lys Met Leu Ile Ala Arg Gly Thr Asn Val Asp Val Arg Thr
    450                 455                 460

Arg Asp Asn Tyr Thr Ala Leu His Val Ala Val Gln Ser Gly Lys Ala
465                 470                 475                 480

Ser Val Val Glu Thr Leu Leu Gly Ser Gly Ala Asp Ile His Val Lys
                485                 490                 495

Gly Gly Glu Leu Met Asp Gly Glu Thr Cys Leu His Ile Ala Ala Arg
            500                 505                 510

Ser Gly Asn Lys Asp Ile Met Leu Leu Leu Asp Glu Asn Ala Asp Ser
        515                 520                 525

Lys Ile Ser Ser Lys Ile Gly Glu Thr Pro Leu Gln Val Ala Ala Lys
    530                 535                 540

Ser Cys Asn Phe Glu Ala Ala Ser Met Ile Leu Lys His Leu Ser Glu
```

```
                                      -continued
545                 550                 555                 560
Val Leu Thr Gln Glu Gln Leu Lys Glu His Val Asn His Arg Thr Asn
                565                 570                 575
Asp Gly Phe Thr Ala Leu His Tyr Ala Ala Glu Ile Glu Gln Arg Gln
                580                 585                 590
Leu His Phe Pro Gly Glu Asp Ala Lys Leu Val Asn Leu Leu Ile Asp
                595                 600                 605
Tyr Gly Gly Met Val Glu Met Pro Ser Leu Asn Ala Asn Glu Thr Ala
                610                 615                 620
Met His Met Ala Ala Arg Ser Gly Asn Gln Ala Val Leu Leu Ala Met
625                 630                 635                 640
Val Asn Lys Ile Gly Ala Gly Ala Val Gln Ile Val Gln Asn Lys Gln
                645                 650                 655
Ser Lys Asn Gly Trp Ser Pro Leu Leu Glu Ala Cys Ala Arg Gly His
                660                 665                 670
Ser Gly Val Ala Asn Ile Leu Leu Lys Val Leu Val Leu Cys Val Gly
                675                 680                 685
Pro Gly Pro Gly Pro Gly Pro Arg Leu Gln Gly Arg Gly Tyr Trp Thr
                690                 695                 700
Arg Thr Arg Ala Arg Val Thr Val Pro Trp Leu Gln Tyr Gln Gly Tyr
705                 710                 715                 720
Trp Ala Arg Thr Arg Thr Arg Thr Arg Ala Arg Ala Thr Gly Pro Gly
                725                 730                 735
Leu Gln Asp Gln Gly Tyr Trp Ala Arg Thr Arg Thr Arg Thr Lys Val
                740                 745                 750
Thr Val Pro Arg Leu Leu Gly Asp His His Ala Arg Ile Asp Val Phe
                755                 760                 765
Asp Glu Met Gly Arg Thr Ala Leu His Leu Ala Ala Phe Asn Gly His
                770                 775                 780
Leu Ser Leu Val His Leu Leu Gln His Lys Ala Phe Val Asn Ser
785                 790                 795                 800
Lys Ser Lys Thr Gly Glu Ala Pro Leu His Leu Ala Ala Gln His Gly
                805                 810                 815
His Val Lys Val Val Asn Val Leu Val Gln Asp His Gly Ala Ala Leu
                820                 825                 830
Glu Ala Ile Thr Leu Asp Asn Gln Thr Ala Leu His Phe Ala Ala Lys
                835                 840                 845
Phe Gly Gln Leu Ala Val Ser Gly Thr Leu Leu Ala Leu Gly Ala Asn
                850                 855                 860
Pro Asn Ala Arg Asp Asp Lys Gly Gln Thr Pro Leu His Leu Ala Ala
865                 870                 875                 880
Glu Asn Asp Phe Pro Asp Val Val Lys Leu Phe Leu Lys Met Arg Asn
                885                 890                 895
Asn Asn Arg Ser Val Leu Thr Ala Ile Asp His Asn Gly Phe Thr Cys
                900                 905                 910
Ala His Ile Ala Ala Met Lys Gly Ser Leu Ala Val Val Arg Glu Leu
                915                 920                 925
Met Met Ile Asp Lys Pro Met Val Ile Gln Ala Lys Thr Lys Thr Leu
                930                 935                 940
Glu Ala Thr Thr Leu His Met Ala Ala Gly Gly His Ala Asn Ile
945                 950                 955                 960
Val Lys Ile Leu Leu Glu Asn Gly Ala Asn Ala Glu Asp Glu Asn Ser
                965                 970                 975
```

```
Gly Met Thr Ala Leu His Leu Gly Ala Lys Asn Gly Phe Ile Ser Ile
            980                 985                 990

Leu Glu Ala Phe Asp Lys Ile Leu Trp Lys Arg Cys Ser Arg Lys Thr
        995                 1000                1005

Gly Leu Asn Ala Leu His Ile Ala Ala Phe Tyr Gly Asn Ser Asp Phe
    1010                1015                1020

Val Asn Glu Met Leu Lys His Val Gln Ala Thr Val Arg Ser Glu Pro
1025                1030                1035                1040

Pro Ile Tyr Asn His His Val Asn Lys Glu Phe Ser Thr Glu Tyr Gly
            1045                1050                1055

Phe Thr Pro Leu His Leu Ala Ala His Ser Gly His Asp Ser Leu Val
        1060                1065                1070

Arg Met Leu Leu Asn Gln Gly Val Gln Val Asp Ala Thr Ser Thr Thr
    1075                1080                1085

Met Met Ser Glu Lys Glu Lys Glu Arg Ala Lys Asp Leu Leu Asn Val
1090                1095                1100

Ala Val Phe Ser Glu Asn Met Ala Val Glu Leu Leu Ile Thr Ala Thr
1105                1110                1115                1120

Glu Tyr Asn Ala Ala Leu Leu Leu Lys Ala Lys Asp Asn Arg Gly Arg
            1125                1130                1135

Pro Leu Leu Asp Val Leu Ile Glu Asn Glu Gln Lys Glu Val Val Ser
        1140                1145                1150

Tyr Ala Ser Val Gln Arg Tyr Leu Thr Glu Val Trp Thr Ala Arg Val
    1155                1160                1165

Asp Trp Ser Phe Gly Lys Phe Val Ala Phe Ser Leu Phe Val Leu Ile
    1170                1175                1180

Cys Pro Pro Ala Trp Phe Tyr Phe Ser Leu Pro Leu Asp Ser Arg Ile
1185                1190                1195                1200

Gly Arg Ala Pro Ile Ile Lys Phe Val Cys His Ile Val Ser His Val
            1205                1210                1215

Tyr Phe Thr Ile Leu Leu Thr Ile Val Val Leu Asn Ile Thr His Lys
        1220                1225                1230

Tyr Glu Val Thr Ser Val Val Pro Asn Pro Val Glu Trp Leu Leu Leu
    1235                1240                1245

Leu Trp Leu Ser Gly Asn Leu Val Ser Glu Leu Ser Thr Val Gly Gly
    1250                1255                1260

Gly Ser Gly Leu Gly Ile Val Lys Val Leu Ile Leu Val Leu Ser Ala
1265                1270                1275                1280

Met Ala Ile Ala Val His Val Leu Ala Phe Leu Leu Pro Ala Val Phe
            1285                1290                1295

Leu Thr His Leu Asp Asn Asp Glu Lys Leu His Phe Ala Arg Thr Met
        1300                1305                1310

Leu Tyr Leu Lys Asn Gln Leu Phe Ala Phe Ala Leu Leu Phe Ala Phe
    1315                1320                1325

Val Glu Tyr Leu Asp Phe Leu Thr Val His His Leu Phe Gly Pro Trp
1330                1335                1340

Ala Ile Ile Ile Met Tyr Asp Leu Ala Arg Phe Leu Val Ile Leu Met
1345                1350                1355                1360

Leu Phe Val Ala Gly Phe Thr Leu His Val Thr Ser Ile Phe Gln Pro
            1365                1370                1375

Ala Tyr Gln Pro Val Asp Glu Asp Ser Ala Glu Leu Met Arg Leu Ala
        1380                1385                1390
```

```
Ser Pro Ser Gln Thr Leu Glu Met Leu Phe Phe Ser Leu Phe Gly Leu
    1395                1400                1405

Val Glu Pro Asp Ser Met Pro Pro Leu His Leu Val Pro Asp Phe Ala
1410                1415                1420

Lys Ile Ile Leu Lys Leu Leu Phe Gly Ile Tyr Met Met Val Thr Leu
1425                1430                1435                1440

Ile Val Leu Ile Asn Leu Leu Ile Ala Met Met Ser Asp Thr Tyr Gln
            1445                1450                1455

Arg Ile Gln Ala Gln Ser Asp Lys Glu Trp Lys Phe Gly Arg Ala Ile
        1460                1465                1470

Leu Ile Arg Gln Met Asn Lys Lys Ser Ala Thr Pro Ser Pro Ile Asn
    1475                1480                1485

Met Leu Thr Lys Leu Ile Ile Val Leu Arg Val Ala Trp Arg Asn Arg
1490                1495                1500

Gly Lys Ala Pro Leu Ser Thr Pro Leu Ala Ser Phe Arg Cys Met Thr
1505                1510                1515                1520

Arg Lys Ala Gln Asp Asp Leu Arg Phe Glu Glu Asn Ile Asp Ala Phe
            1525                1530                1535

Ser Met Gly Gly Gly Gln Gln Gly Arg Gln Ser Pro Thr Asn Glu Gly
        1540                1545                1550

Arg Gly Gln Gln Glu Leu Gly Asn Ser Ala Asp Trp Asn Ile Glu Thr
    1555                1560                1565

Val Ile Asp Trp Arg Lys Ile Val Ser Met Tyr Tyr Gln Ala Asn Gly
1570                1575                1580

Lys Leu Thr Asp Gly Arg Thr Lys Glu Asp Val Asp Leu Ala Met Ala
1585                1590                1595                1600

Val Pro Thr Ser Phe Ile Lys Pro Gln Gly Pro Asp Thr Thr Cys Arg
            1605                1610                1615

Pro Ile Asp Tyr Thr Trp Leu Arg Leu Cys Lys Thr Lys Ser His Gly
        1620                1625                1630

Ser Gly Leu Ser Ile Val Arg Arg Lys Thr Arg Gly Lys Ile Val Tyr
    1635                1640                1645

Ser Thr Arg Thr Asn Thr Ser Val Leu Gln Ile Asn Ser Ser Arg Asn
1650                1655                1660

Ala Pro Lys Ile Tyr Leu Arg Tyr Gly Arg Ala Lys Ile Ala His Phe
1665                1670                1675                1680

Phe Phe Thr Ser Thr Thr Leu Lys Gly Gly Ala Phe Met Trp His Gly
            1685                1690                1695

Leu Ala Ala Arg Leu Cys Lys Ile Arg Val Asp His Met
        1700                1705

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence:amino acid
      sequence conserved between Drosophila and C.
      elegans encoding degenerate primer sets

<400> SEQUENCE: 7

Leu Asp Val Leu Ile Glu Asn Glu Gln Lys Glu Val
 1               5                  10

<210> SEQ ID NO 8
<211> LENGTH: 11
<212> TYPE: PRT
```

```
<213> ORGANISM: Artificial Sequence
<220> FEATURE:
<223> OTHER INFORMATION: Description of Artificial Sequence:amino acid
      sequence conserved between Drosophila and C.
      elegans encoding degenerate primer sets

<400> SEQUENCE: 8

His His Leu Phe Gly Pro Trp Ala Ile Ile Ile
  1               5                  10

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence:amino acid
      sequence conserved between Drosophila and C.
      elegans encoding degenerate primer sets

<400> SEQUENCE: 9

Val Leu Ile Asn Leu Leu Ile Ala Met Met Ser Asp Thr Tyr Gln Arg
  1               5                  10                  15

Ile Gln

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:nompC
      transmembrane domain (channel region) #1

<400> SEQUENCE: 10

Ile Leu Leu Leu Leu Val Ala Phe Ile Val Cys Pro Pro Val Trp Ile
  1               5                  10                  15

Gly Phe Thr

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:nompC
      transmembrane domain (channel region) #2

<400> SEQUENCE: 11

Tyr Trp Tyr Glu Val Gly Leu Leu Ile Trp Leu Ser Gly Leu Leu Leu
  1               5                  10                  15

Phe Glu Leu Thr
             20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:nompC
      transmembrane domain (channel region) #3

<400> SEQUENCE: 12

Ile Lys Val Leu Val Leu Leu Leu Gly Met Ala Gly Val Gly Val His
  1               5                  10                  15

Val Ser Ala Phe
             20
```

```
<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence:nompC
      transmembrane domain (channel region) #4

<400> SEQUENCE: 13

Thr Leu Val Tyr Cys Arg Asn Gln Cys Phe Ala Leu Ala Phe Leu Leu
 1               5                  10                  15

Ala Cys Val Gln Ile Leu Asp Phe Leu
            20                  25

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:nompC
      transmembrane domain (channel region) #5

<400> SEQUENCE: 14

Phe Leu Ala Val Leu Ala Ile Phe Val Phe Gly Phe Ser Met His Ile
 1               5                  10                  15

Val Ala Leu Asn
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence:nompC
      transmembrane domain (channel region) #6

<400> SEQUENCE: 15

Ile Val Phe Gly Ile Tyr Met Leu Val Ser Val Val Leu Ile Asn
 1               5                  10                  15

Leu Leu Ile Ala Met Met Ser
            20

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence:nompC
      transmembrane domain (channel region) #7

<400> SEQUENCE: 16

Tyr Ile Asn Phe Ile Leu His Cys Val Leu Ile Ile Leu Tyr Phe Ser
 1               5                  10                  15

Ile

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence:nompC
      transmembrane domain (channel region) #8

<400> SEQUENCE: 17
```

```
Ile Tyr Leu Met Ile His Leu Ser Ile Val Gly Ile Thr Pro Ile Tyr
  1               5                  10                  15
Pro Val Leu
```